United States Patent [19]

Oinuma et al.

[11] Patent Number: 5,179,095
[45] Date of Patent: Jan. 12, 1993

[54] PIPERIDINE DERIVATIVE AND PHARMACEUTICAL COMPOSITION CONTAINING THE SAME

[75] Inventors: Hitoshi Oinuma, Sakuramura; Motosuke Yamanaka, Abiko; Kazutoshi Miyake, Ushiku; Tomonori Hoshiko, Tsuchiura; Norio Minami, Sakuramura; Tadao Shoji, Kukizakimachi; Yoshiharu Daiku, Sakuramura; Kohei Sawada, Toride; Kenichi Nomoto, Tsuchiura, all of Japan

[73] Assignee: Eisai Co., Ltd., Tokyo, Japan

[21] Appl. No.: 798,963

[22] Filed: Nov. 26, 1991

Related U.S. Application Data

[62] Division of Ser. No. 594,079, Oct. 9, 1990, Pat. No. 5,118,689, which is a division of Ser. No. 408,106, Sep. 15, 1989, Pat. No. 4,996,215, which is a division of Ser. No. 16,035, Feb. 18, 1987, Pat. No. 4,876,262.

[30] Foreign Application Priority Data

Feb. 26, 1986 [JP] Japan .................. 61-39270

[51] Int. Cl.$^5$ .................. A61K 31/50; A61K 31/505; C07D 401/06; C07D 403/06
[52] U.S. Cl. .................. 514/249; 514/252; 514/255; 514/256; 514/274; 544/238; 544/312; 544/335; 544/336; 544/353; 544/354; 544/355; 544/406; 544/408
[58] Field of Search .................. 544/353, 238, 335, 312, 544/354, 355, 406, 408, 336; 514/252, 269, 249, 274, 256, 255

[56] References Cited

U.S. PATENT DOCUMENTS

| 2,682,544 | 6/1954 | Archer | 260/294.8 |
| 4,117,151 | 9/1978 | Descamps et al. | 544/376 X |
| 4,244,963 | 1/1981 | Grier et al. | 546/182 |

FOREIGN PATENT DOCUMENTS

| 0158775 | 10/1985 | European Pat. Off. |
| 62-153268 | 7/1987 | Japan . |
| 2067562 | 7/1991 | United Kingdom . |

*Primary Examiner*—Joseph Paul Brust
*Attorney, Agent, or Firm*—Flynn, Thiel, Boutell & Tanis

[57] ABSTRACT

A new piperidine compound is pharmacologically effective for treatment of the arrythmia and is defined by the formula:

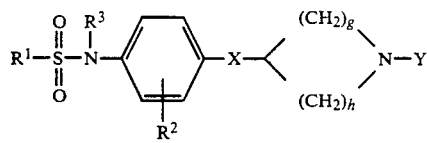

in which $R^1$ is a lower alkyl or a tolyl, $R^2$ is hydrogen, hydroxyl, a lower alkoxy or a lower alkyl, $R^3$ is hydrogen, a lower alkyl, a lower alkenyl, a cycloalkyl or a cycloalkylalkyl, X is —CO—, —CH$^2$— or —CHOH—, g is an integer of 1 to 3, h is an integer of 1 to 3, Y is hydrogen, a lower alkyl, a lower alkenyl, cyano, CH$^2$COOR, R being hydrogen or a lower alkyl, a cycloalkyl, a cycloalkylalkyl,

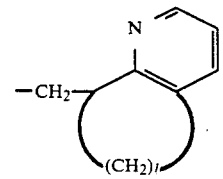

l being 1 or 2, —A—B, A being —(CH$_2$)$_n$—, n being an integer of 1 to 5,
a straight-chain alkylene group having 1 to 5 carbon atoms which is a divalent group derived from a straight-chain alkane having lower alkyl, phenyl or hydroxyl group(s) bonded directly to one or more carbon atoms constituting said alkane by removing a hydrogen atom bonded to each of the carbon atoms placed at both ends thereof,
a straight-chain alkylene group having 1 to 5 carbon atoms which is a divalent group derived from a straight-chain alkene having a double bond formed between carbon atoms adjacent to each other by removing a hydrogen atom bonded to each of the carbon atoms placed at both ends thereof,
—(CH$_2$)$_k$—S—, k being an integer of 2 to 5, —(CH$_2$)$_p$—CO—, p being an integer of 1 to 4, B being cyano, —NR$_4$R$_5$, a heterocyclic ring or a condensed aromatic ring.

8 Claims, No Drawings

PIPERIDINE DERIVATIVE AND PHARMACEUTICAL COMPOSITION CONTAINING THE SAME

This is a division of Ser. No. 07/594 079, filed Oct. 9, 1990, now U.S. Pat. No. 5,118,689 which is a division of Ser. No. 07/408 106, filed Sep. 15, 1989, now U.S. Pat. No. 4,996,215, issued Feb. 26, 1991, which is a divison of Ser. No. 07/016 035, filed Feb. 18, 1987, now U.S. Pat. No. 4,876,262, issued Oct. 24, 1989.

The present invention relates to piperidine derivatives and pharmacologically acceptable salts thereof having excellent medicinal effects, processes for producing them and medicines containing them.

PRIOR ART

Arrhythmias often occur as complications to cardiac diseases such as myocardial infarction and heart failure. In a serious case, arrhythmias give rise to a ventricular fibrillation to cause sudden death.

Although various antiarrythmic agents are now available on the market, those having both satisfactory effects and high safety have not been obtained yet. For example, antiarrythmic agents of Class I according to the classification of Vaughan-Williams which cause a selective inhibition of the maximum velocity of the upstroke of the action potential (Vmax) have only insufficient effects for preventing the ventricular fibrillation. In addition, they have problems regarding safety, namely, they cause a depression of the myocardial contractility and have a tendency to induce arrhythmia due to an inhibition of the impulse conduction. Beta-adrenoceptor blockers and calcium antagonists which belong to Class II and IV respectively, have a defect that their effects are either limited to a certain type of arrhythmia or are unreliable, though their safety is higher than that of the antiarrhythmic agents of Class I.

Antiarrhythmic agents of Class III are drugs which cause a selective prolongation of the duration of the action potential without a significant depression of the Vmax. Although there has been no available drug which possess pure and potent properties of Class III antiarrhythmics, drugs of this class are expected to be effective in preventing ventricular fibrillations. Moreover, they are, by definition, not considered to cause a myocardial depression or an induction of arrhythmias due to the inhibition of the action potential conduction as seen with Class I antiarrhythmic agents.

Under these circumstances, the development of pure and potent antiarrhythmic agents of Class III has been awaited.

SUMMARY OF THE INVENTION

An object of the present invention is to provide new piperidine derivatives and pharmacologically acceptable salts thereof, processes for producing the piperidine derivatives and pharmacologically acceptable salts thereof and medicines containing said piperidine derivative or pharmacologically acceptable salts thereof as the active ingredient.

The invention provides a new piperidine derivative, an analogous compound thereto, however having a heterocyclic ring other than the piperidine ring and a pharmacologically acceptable salt thereof. These compounds have the formula shown below.

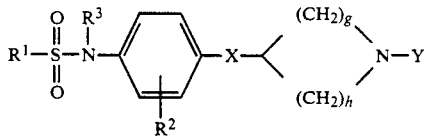

in which R1 is a lower alkyl or a tolyl, R2 is hydrogen, hydroxyl, a lower alkoxy or a lower alkyl, R3 is hydrogen, a lower alkyl, a lower alkenyl, a cycloalkyl or a cycloalkylalkyl, X is —CO—, —CH$_2$— or —CHOH—, g is an integer of 1 to 3, h is an integer of 1 to 3, Y is hydrogen, a lower alkyl, a lower alkenyl, cyano, —CH$_2$COOR, R being hydrogen or a lower alkyl, a cycloalkyl, a cycloalkylalkyl,

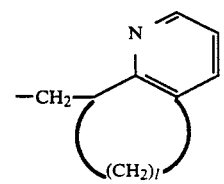

l being 1 or 2, -A-B, A being —(CH$_2$)n—, n being an integer of 1 to 5,
a straight-chain alkylene group having 1 to 5 carbon atoms which is a divalent group derived from a straight-chain alkane having lower alkyl, phenyl or hydroxyl group(s) bonded directly to one or more carbon atoms constituting said alkane by removing a hydrogen atom bonded to each of the carbon atoms located at both ends thereof,
a straight-chain alkenylene group having 2 to 5 carbon atoms which is a divalent group derived from a straight-chain alkene having a double bond formed between carbon atoms adjacent to each other by removing a hydrogen atom bonded to each of the carbon atoms located at both ends thereof,
—(CH$_2$)$_k$—S—, k being an integer of 2 to 5, —(CH$_2$)$_p$— p being an integer of 1 to 4, B being cyano, —NR$^4$R$^5$

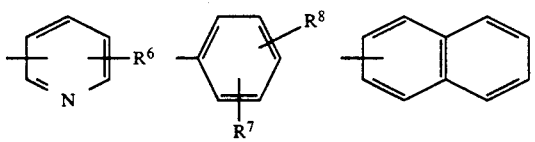

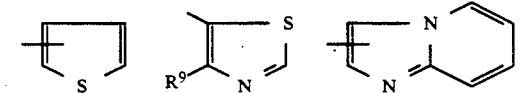

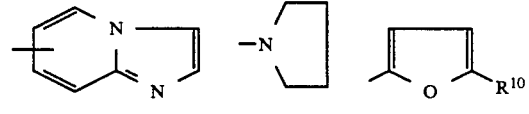

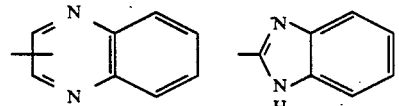

-continued

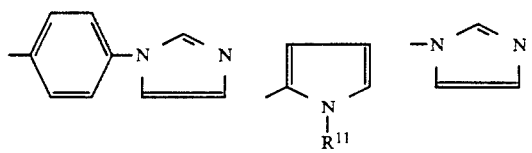

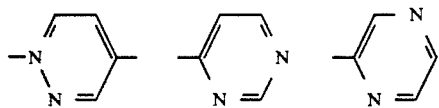

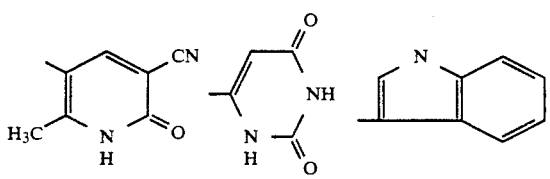

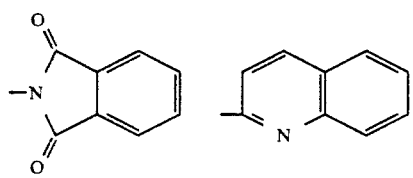

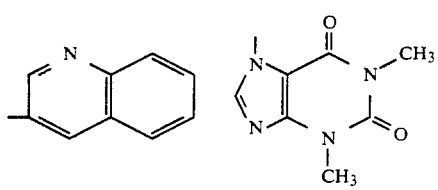

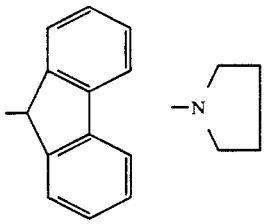

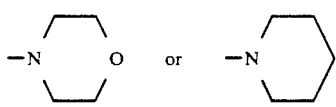

$R^4$ and $R^5$ each being hydrogen or a lower alkyl, $R^6$ being hydrogen, a lower alkyl, a lower alkoxy, cyano, imidazolyl, hydroxyl or a halogen, $R^7$ and $R^8$ each being hydrogen, a halogen, a lower alkyl, a lower alkoxy or methanesulfonamido, $R^9$ $R^{10}$ and $R^{11}$ each being hydrogen or a lower alkyl.

Then are preferably proposed embodiments where g and h each are 2; g is 3 and h is 1; g is 2 and h is 3; g is 1 and h is 2; and g is 1 or 2 and h is 2 or 3.

The lower alkyl group for $R^1$, $R^2$, $R^3$, $R^4$, $R^5$, $R^6$, $R^7$, $R^8$, $R^9$, $R^{10}$, $R^{11}$ and A is preferred to have 1 to 6 carbon atoms, being either straight or branched, such as methyl, ethyl, n-propyl, n-butyl, isopropyl, isobutyl, 1-methylpropyl, tert-butyl, n-pentyl, 1-ethylpropyl, isoamyl and n-hexyl. The lower alkoxy for $R^2$, $R^6$, $R^7$ and $R^8$ is preferred to be one derive from the above defined alkyl. The halogen for $R^6$, $R^7$ and $R^8$ is preferred to be chlorine, bromine, iodine or fluorine.

The term "a straight-chain alkylene group having 1 to 5 carbon atoms which is a divalent group derived from a straight-chain alkane having lower alkyl, phenyl or hydroxyl group(s) bonded directly to one or more carbon atoms constituting said alkane by removing a hydrogen atom bonded to each of the carbon atoms located at both ends thereof" in the definition of A means a divalent group derived from a straight-chain alkane having lower alkyl such as methyl, phenyl or hydroxyl group(s) bonded to terminal carbon atoms or other carbon atoms by removing a hydrogen atom from each of the terminal carbon atoms. Preferred examples of these groups include a group of the formula:

a group of the formula:

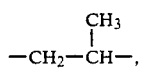

a group of the formula:

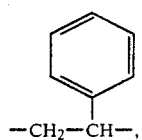

a group of the formula:

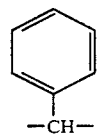

and a group of the formula:

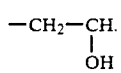

The term "a straight chain alkenylene group having 2 to 5 carbon atoms which is a divalent group derived from a straight-chain alkene having a double bond formed between carbon atoms adjacent to each other by removing a hydrogen atom bonded to each of the carbon atoms located at both ends thereof" means, for example, a group of the formula: $-CH_2-CH=CH-$ and a group of the formula: $-CH_2-CH_2-CH=CH-$.

The pharmacologically acceptable salts include inorganic acid salts such as hydrochlorides, sulfates, hydrobromides, perchlorates and hydriodides and organic acid salts such as oxalates, maleates, fumarates, succinates and methanesulfonates.

The intended compounds (I) or pharmacologically allowable salts thereof of the present invention having an excellent antiarrhythmic activity and a high safety can be used as antiarrhythmic agents. In addition, the effects of these compounds on intractable arrythmia or arrythmia on which other medicines are ineffective are expectable.

PRODUCTION PROCESSES

The compounds (I) of the present invention can be produced by various processes. Typical examples of the processes are as follows:

PRODUCTION PROCESS A

Production process A

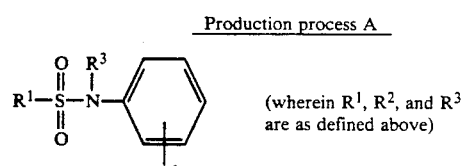
(wherein $R^1$, $R^2$, and $R^3$ are as defined above) (II)

Step 1 ↓

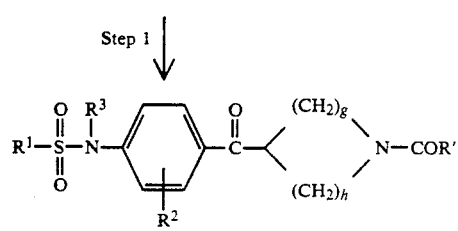 (III)

Step 2 | hydrolysis

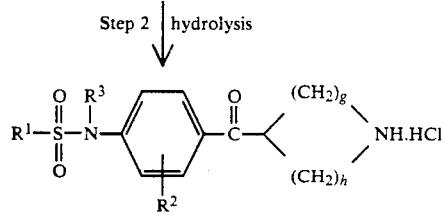 (IV)

Step 3   Z—Y' (wherein Z represents a halogen atom such as a chlorine, bromine or iodine atom or a free group such as a methanesulfonyloxy or p-toluene-sulfonyloxy group and $\underline{n}$ is as defined above) Y' is defined above except for hydrogen excluded.

or

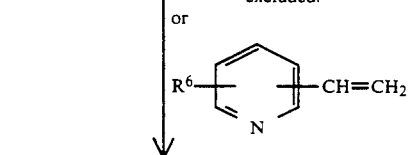 (VI)

↓

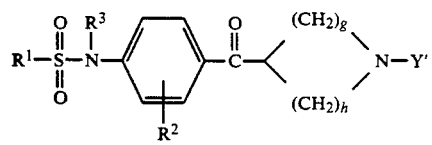 (VII)

step 4 of reduction ↙    step 5 of reduction ↘

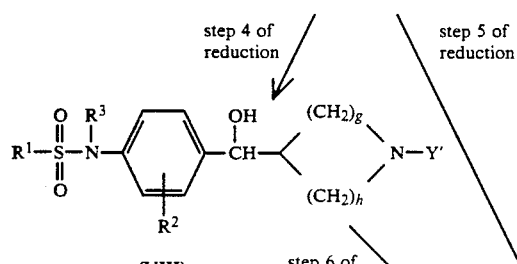

(VIII)

step 6 of reduction ↘

-continued
Production process A

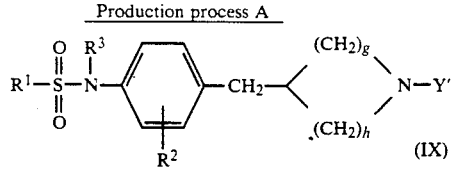 (IX)

PRODUCTION PROCESS B

The intended compounds of the above general formula in which $R^3$ is a lower alkyl, a lower alkenyl, or a cycloalkyl can be produced as shown below.

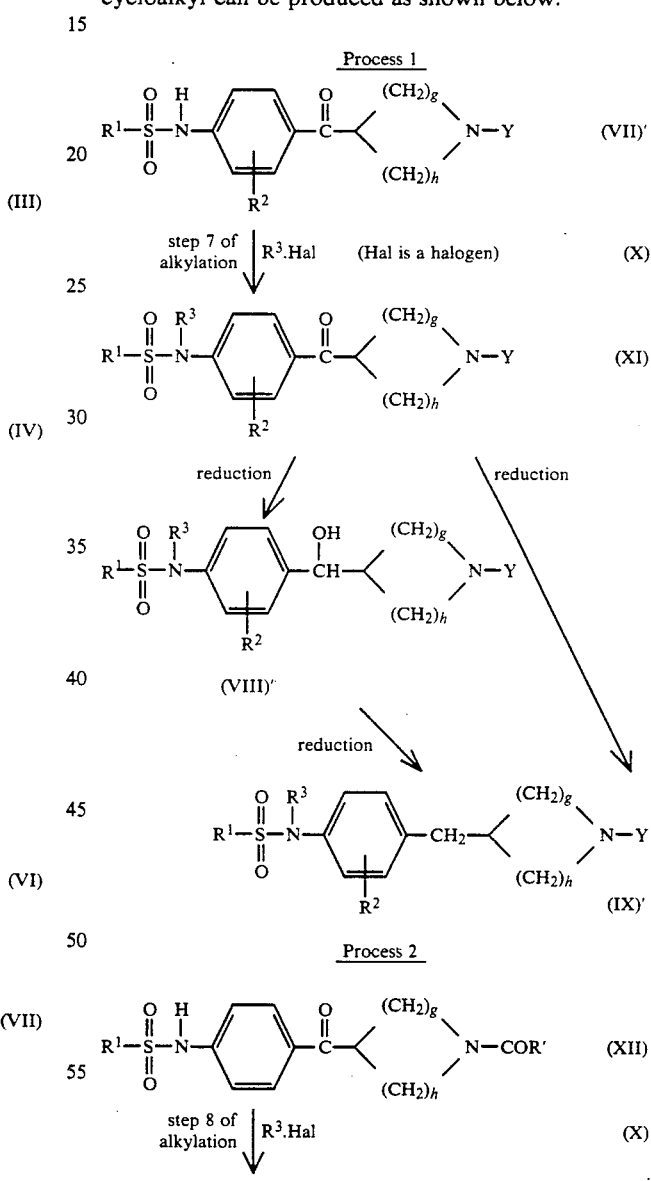

PRODUCTION PROCESS C

The compounds of the above general formula (I) in which Y is H and X is a group of the formula:

can be produced by directly reducing the above-mentioned compound (IV), omitting the step 3, to obtain the compound (XIII). The reduction is conducted in the same way as shown in the step 4.

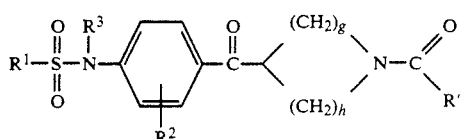 (XIII)

PROCESS D

The compound in which X is —CH²— in the formula (I) is produced below.

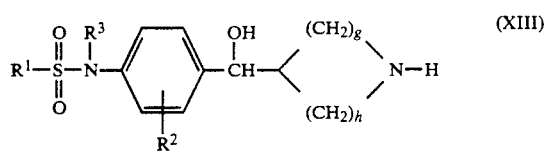 (III)

↓ step 9 of reduction

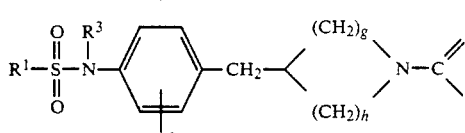 (XIV)

↓ step 10 of hydrolysis

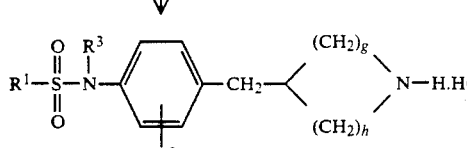 (XV)

↓ step 11 of alkylation

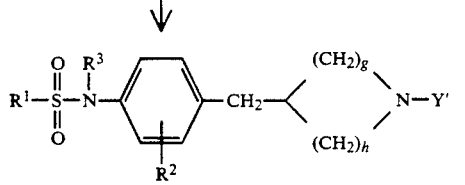 (IX)

PROCESS E

The process A provides the invention compound in the step 3. The invention compound is also produced by each below shown method when Y is one of the followings.

METHOD E-1

A compound in which A is —CH²— and B is

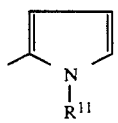 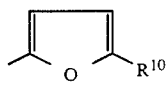

is produced. A compound in which A is $$-CH_2C- \atop \| \atop CH_2$$

and B is

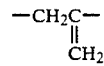

is produced. This B is called $Y^2$.

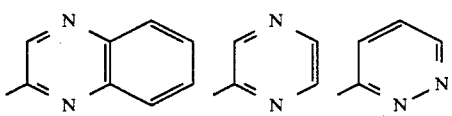 (XVII)

HCHO and (XVIII)

step 12

(XIV)

or (XX)

↓

(XXI)

METHOD E-2

A compound in which A is —(CH²)2— and B is is produced below. This -A-B is called $Y^3$.

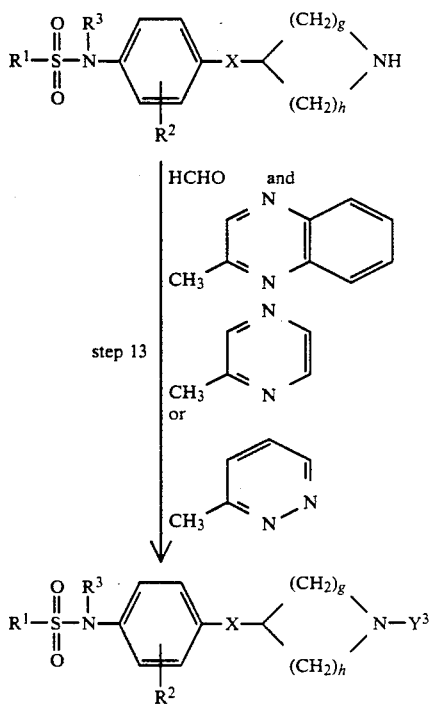

Each above shown step is conducted as described below in detail.

STEP 1

A sulfonanilide derivative (II) is reacted, according to the Friedel-Crafts reaction, with a reactive acid derivative such as a halogenate or anhydride of a carboxylic acid having the following formula:

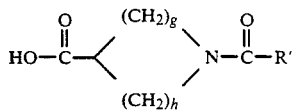

in which R' is a lower alkyl or phenyl and g and h are defined above, in the presence of a Lewis acid such as aluminum chloride, tin chloride and zinc chloride in an inert solvent such as carbon disulfide, dichloromethane, chloroform and nitrobenzene to form a corresponding anilide derivative (III).

STEP 2

The acetyl group of the compound (III) obtained in the step 1 is hydrolyzed in this step. The hydrolysis is effected in, for example, a dilute aqueous alkali solution or dilute aqueous mineral acid solution. In a preferred embodiment, the hydrolysis is effected in 2 to 6N hydrochloric acid under reflux or in a 0.5 to 3N aqueous solution of sodium hydroxide under reflux.

STEP 3

(1) in case Y is other than hydrogen, that is, Y is Y'

The compound (IV) of the step 2 is normally condensed with a compound having the formula: Z-Y' (V), such as Z-A-B and

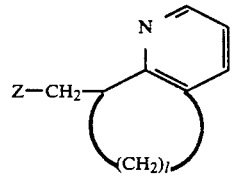

in which Z is a group to eliminate and is a halogen such as chlorine, bromine and iodine, methansulfonyloxy and p-toluenesulfonyloxy.

In a preferred embodiment of this process, the reaction is carried out in the presence of a deacidifying agent such as potassium carbonate or sodium carbonate and potassium iodide (used when Z is not iodine) in a solvent such as N,N-dimethylformamide, dimethyl sulfoxide, acetonitrile, acetone, butanol, propanol, ethanol or methanol at a temperature of about 50° to 120° C. to obtain the compound (VII).

(2) A compound in which A is —($CH^2$)2— and B is

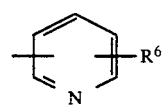

is produced below. The reaction in detail is illustrated below.

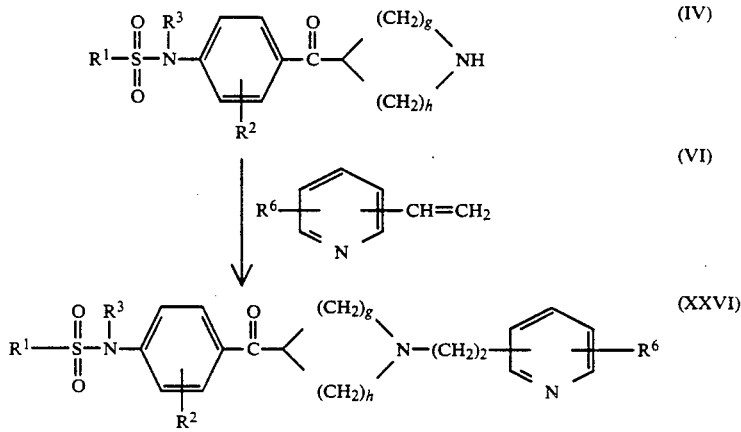

More particularly, an unsubstituted or substituted vinylpyridine (VI) is reacted with the compound (free base) (IV) obtained in the above-mentioned step 2 or pharmacologically acceptable acid-addition salt thereof in a lower alkyl alcohol such as methanol, ethanol or propanol or a mixture thereof with water at a temperature ranging from room temperature to about 100° C. to obtain the intended compound (XXVI). When a free base is used as the starting material in this process, preferred results are obtained by using an acidic catalyst such as acetic or hydrochloric acid or an alkali metal catalyst such as sodium.

In the steps 4 to 6, the compound (VII) obtained in the step 3 is reduced to fproduce the compounds (VIII) or (IX).

STEP 4

The compound (VII) prepared in the step 3 is reduced in this step. The reduction is effected by an ordinary method wherein, for example, the compound (VII) is treated with sodium borohydride or lithium borohydride in a solvent such as methanol, ethanol, 2-propanol, dimethylformamide or dimethyl sulfoxide at a temperature ranging from about $-10°$ C. to room temperature to obtain the intended alcohol (VIII) of the present invention.

STEP 5

An arylketone compound (VII) is reacted with two or more equivalents of a trialkylsilane, preferably triethylsilane, in an excess of trifluoroacetic acid, at a temperature ranging from room temperature to 100° C. for several days to produce the compound (IX). Dichloroethane, carbon tetrachloride, chloroform, dichloromethane and acetonitrile are also used as a solvent.

STEP 6

An alcohol compound (VIII) obtained in the same way as shown in the step 4 is treated with an acid, preferably with 20% sulfuric acid-acetic acid for a short time to obtain a dehydrate and the dehydrate is catalytically hydrogenated to produce the compound (IX).

STEP 7

The compound (VII)″ of the above general formula (I) wherein $R^3$ is H is N-alkylated in this step. The compound (VII)″ is reacted with an alkyl halide of the formula (X) in the presence of a base in a solvent such as dimethylformamide, dimethyl sulfoxide, a lower alkyl alcohol, e.g. methanol, ethanol or propanol, or acetone at a reaction temperature of about 50° to 120° C. to obtain the intended compound (XI). The bases used in this step include, for example, potassium carbonate, sodium carbonate, sodium hydrogencarbonate, sodium ethoxide, sodium methoxide and sodium hydride.

When 2 mole equivalents or more of $R^3HAL$ (X) is used, dialkylation, alkenylation for di-lower alkenyl and alkylation for dicycloalkyl may be carried out as far as Y is hydrogen. Similarly the step 8 of the process B can be conducted for N-alkylation.

The compound (XI) obtained is reduced in the same was as shown in the steps 4 to 6 to further obtain the compound (VIII)' or (IX)'.

STEPS 9 TO 11

Each step is conducted in the same way as shown the step 5 (reduction), the step 2 (hydrolysis) and the steps 7 and 8 (alkylation).

STEP 12

A secondary amine (XVII) is converted to a tertiary amine (XXI) by the Mannich reaction. An active hydrogen-having compound, such as a furan compound, a pyrrole compound and a nitrogen-including heterocyclic compound having a methyl group, is condensed with an amine and formaldehyde or para-formaldehyde, preferably in a solvent such as water and an alcohol, under the acidic condition with acetic acid or hydrochloric acid, at a temperature ranging from room temperature to 100° C.

STEP 13

A secondary amine is alkylated by the Mannich reaction. The reaction proceeds in the same way as shown in the step 12. It is also possible that the secondary amine is used in the form of hydrochloric acid salt, not a free acid, to produce the compound (XXV).

The piperidine derivative obtained above can be converted to a pharmacologically acceptable salt thereof by a conventional method.

To facilitate the understanding of the present invention, typical examples of the compounds of the present invention will be shown below, which by no means limit the invention. The compounds are shown in their free form.

1. 4-(4-methylsulfonylaminobenzoyl)-1-[2-(3-pyridyl)ethyl]piperidine,
2. 4-(4-methylsulfonylaminobenzoyl)-1-(4-pyridyl)methylpiperidine,
3. 4-(4-methylsulfonylaminobenzoyl)-1-[3-(4-pyridyl)propyl]piperidine,
4. 1-(6-methyl-3-pyridyl)methyl-4-(4-methylsulfonylaminobenzoyl)piperidine
5. 4-(4-methylsulfonylaminobenzoyl)-1-[2-(4-pyridyl)ethyl]piperidine,
6. 1-[2-(3,4-dimethoxyphenyl)ethyl]-4-(4-methylsulfonylaminobenzoyl)piperidine,
7. 4-(4-methylsulfonylaminobenzoyl)-1-[4-(3-pyridyl)butyl]piperidine,
8. 4-(4-methylsulfonylaminobenzoyl)-1-[2-(4-pyridylthio)ethyl]piperidine,
9. 4-(4-methylsulfonylaminobenzoyl)piperidine,
10. 4-(4-methylsulfonylaminobenzoyl)-1-[3-(3-pyridyl)propyl]piperidine,
11. 4-(4-methylsulfonylaminobenzoyl)-1-[5-(3-pyridyl)pentyl]piperidine,
12. 1-(6-chloro-3-pyridyl)methyl-4-(4-methylsulfonylaminobenzoyl)piperidine,
13. 4-(4-methylsulfonylaminobenzoyl)-1-[2-(2-pyridyl)ethyl]piperidine,
14. 4-(4-methylsulfonylaminobenzoyl)-1-(2-phenylethyl)piperidine,
15. 4-(2-hydroxy-4-methylsulfonylaminobenzoyl)-1-(4-pyridyl)methylpiperidine,
16. 4-(2-hydroxy-4-methylsulfonylaminobenzoyl)-1-(2-phenylethyl)piperidine,
17. 4-(4-methylsulfonylaminobenzoyl)-1-(3-pyridyl)methylpiperidine,
18. 4-(4-methylsulfonylaminobenzoyl)-1-(2-pyridyl)methylpiperidine,
19. 4-(4-methylsulfonylaminobenzoyl)-1-nicotinoylmethylpiperidine,
20. 4-(4-methylsulfonylaminobenzoyl)-1-[2-(2-thienyl)ethyl]piperidine 21. 4-(4-methylsulfonylaminophenyl)-hydroxymethyl-1-(2-(2-pyridyl)ethyl)piperidine
22. 4-(2-methoxy-4-methylsulfonylaminobenzoyl)-1-(4-pyridyl)methylpiperidine,
23. 1-[2-(4-chlorophenyl)ethyl]-4-(4-methylsulfonylaminobenzoyl)piperidine,
24. 1-[2-(4-methoxyphenyl)ethyl]-4-(4-methylsulfonylaminobenzoyl)piperidine,
25. 4-(4-methylsulfonylaminobenzoyl)-1-[3-(3-pyridyl)-2-propenyl]piperidine,
26. 4-(4-ethylsulfonylaminobenzoyl)-1-(4-pyridyl)methylpiperidine,
27. 4-(4-ethylsulfonylaminobenzoyl)-1-(2-phenylethyl)-piperidine,
28. 1-benzyl-4-(4-methylsulfonylaminobenzoyl)piperidine,
29. 1-[2-(4-fluorophenyl)ethyl]-4-(4-methylsulfonylaminobenzoyl)piperidine,
30. 4-(4-methylsulfonylaminobenzoyl)-1-(3-phenylpropyl)piperidine,
31. 4-(4-methylsulfonylaminobenzoyl)-1-(2-thienylmethyl)methylpiperidine,
32. 1-[2-(4-hydroxyphenyl)ethyl]-4-(4-methylsulfonylaminobenzoyl)piperidine,
33. 1,4-di(4-methylsulfonylaminobenzoyl)piperidine,
34. 1-[6,7-dihydro-5H-7-cyclopenta[b]pyridinyl]methyl-4-(4-methylsulfonylaminobenzoyl)piperidine,
35. N-methyl-4-(4-methylsulfonylaminobenzoyl)-1-[2-(3-pyridyl)ethyl]piperidine,
36. N-butyl-4-(4-methylsulfonylaminobenzoyl)-1-[2-(3-pyridyl)ethyl]piperidine,
37. 4-(4-methylsulfonylaminobenzoyl)-1-[1-(4-pyridyl)ethyl]piperidine,
38. 4-(4-methylsulfonylaminobenzoyl)-1-[1-phenyl-1-(4-pyridyl)methyl]piperidine,
39. 1-[2-(4-methylphenyl)ethyl]-4-(4-methylsulfonylaminobenzoyl)piperidine,
40. 4-(4-methylsulfonylaminobenzoyl)-1-(1-naphthyl)methylpiperidine,
41. 1-[2-hydroxy-2-(4-methylsulfonylaminophenyl)ethyl]-4-(4-methylsulfonylaminobenzoyl)piperidine,
42. 1-[2-hydroxy-2-(3-pyridyl)ethyl]-4-(4-methylsulfonylaminobenzoyl)piperidine,
43. 1-(2-hydroxy-2-phenylethyl)-4-(4-methylsulfonylaminobenzoyl)piperidine,
44. 1-(2-chlorophenyl)methyl-4-(4-methylsulfonylaminobenzoyl)piperidine,
45. 1-[2-(5-ethyl-2-pyridyl)ethyl]-4-(4-methylsulfonylaminobenzoyl)piperidine,
46. 1-[2-(6-methyl-2-pyridyl)ethyl]-4-(4-methylsulfonylaminobenzoyl)piperidine,
47. 1-[2-(6-methyl-3-pyridyl)ethyl]-4-(4-methylsulfonylaminobenzoyl)piperidine,
48. 1-[3-(6-methyl-3-pyridyl)propyl]-4-(4-methylsulfonylaminobenzoyl)piperidine,
49. 1-[1-(3-methoxy-2-pyridyl)methyl]-4-(4-methylsulfonylaminobenzoyl)piperidine,
50. 1-[2-(5-methyl-4-pyridylthio)ethyl]-4-(4-methylsulfonylaminobenzoyl)piperidine,
51. 1-[1-(2-methoxy-5-pyridyl)methyl]-4-(4-methylsulfonylaminobenzoyl)piperidine,
52. 1-[1-(3-hydroxy-2-pyridyl)methyl]-4-(4-methylsulfonylaminobenzoyl)piperidine,
53. 1-[2-(6-ethyl-2-pyridyl)ethyl]-4-(4-methylsulfonylaminobenzoyl)piperidine,
54. 1-[3-(5-ethyl-2-pyridyl)propyl]-4-(4-methylsulfonylaminobenzoyl)piperidine,
55. 1-[4-(5-ethyl-2-pyridyl)butyl]-4-(4-methylsulfonylaminobenzoyl)piperidine,
56. 1-[2-(5-butyl-2-pyridyl)ethyl]-4-(4-methylsulfonylaminobenzoyl)piperidine,
57. 1-[2-(2-methyl-4-pyridyl)ethyl]-4-(4-methylsulfonylaminobenzoyl)piperidine,
58. 1-[2-(2-ethyl-4-pyridyl)ethyl]-4-(4-methylsulfonylaminobenzoyl)piperidine,
59. 1-[2-(2-chloro-5-pyridyl)ethyl]-4-(4-methylsulfonylaminobenzoyl)piperidine,
60. 1-[3-(2-chloro-5-pyridyl)propyl]-4-(4-methylsulfonylaminobenzoyl)piperidine, and
61. 4-(4-methylsulfonylaminobenzoyl)-1-[2-(4-methyl-5-thiazole)ethyl]piperidine.
62. 1-[4-(1-imidazolyl)benzoylmethyl]-4-(4-methylsulfonylaminobenzoyl)piperidine
63. 1-[2-[3-(2-cyano)pyridyl]ethyl]-4-(4-methylsulfonylaminobenzoyl)piperidine
64. 1-[3-[3-(2-cyano)pyridyl]propyl]-4-(4-methylsulfonylaminobenzoyl)piperidine
65. 1-[3-[4-(2-cyano)pyridyl]propyl]-4-(4-methylsulfonylaminobenzoyl)piperidine
66. 1-[2-(1-imidazolyl)-3-pyridylmethyl]-4-(4-methylsulfonylaminobenzoyl)piperidine
67. 1-(5-methyl-2-furanyl)methyl-4-(4-methylsulfonylaminobenzoyl)piperidine
68. 1-(1-methyl-2-pyrrolyl)methyl-4-(4-methylsulfonylaminobenzoyl)piperidine
69. 1-(1-imidazolyl-3-propyl)-4-(4-methylsulfonylaminobenzoyl)piperidine
70. 4-(4-methylsulfonylamino)-1-[2-(3-pyridazinyl)ethyl]piperidine
71. 4-(4-methylsulfonylaminobenzoyl)-1-[2-(4-pyrimidinyl)-2-propenyl]piperidine
72. 4-(4-methylsulfonylaminobenzoyl)-1-(2-pyrazinylmethyl)piperidine
73. 4-(4-methylsulfonylaminobenzoyl)-1-[2-(2-pyrazinyl)ethyl]piperidine
74. 1-[2-(1,2-dihydro-6-methyl-2-oxo-3-pyridinecarbonitril-5-yl)-2-oxoethyl]-4-(4-methylsulfonylaminobenzoyl)piperidine
75. 4-(4-methylsulfonylaminobenzoyl)-1-(6-uracilmethyl)piperidine
76. 1-[2-(3-indolyl)ethyl]-4-(4-methylsulfonylaminobenzoyl)piperidine
77. 4-(4-methylsulfonylaminobenzoyl)-1-(2-phthalimidoethyl)piperidine
78. 4-(4-methylsulfonylaminobenzoyl)-1-(2-quinolylmethyl)piperidine
79. 4-(4-methylsulfonylaminobenzoyl)-1-(3-quinolylmethyl)piperidine
80. 1-(1-imidazo[1,2-a]pyridylmethyl)-4-(4-methylsulfonylaminobenzoyl)piperidine
81. 1-[2-(1-imidazo[1,2-a]pyridyl)ethyl]-4-(4-methylsulfonylaminobenzoyl)piperidine
82. 1-(6-imidazo[1,2-a]pyridylmethyl)-4-(4-methylsulfonylaminobenzoyl)piperidine
83. 1-[2-(3-imidazo[1,2-a]pyridyl)-2-oxoethyl]-4-(4-methylsulfonylaminobenzoyl)piperidine
84. 1-(2-benzimidazolylmethyl)-4-(4-methylsulfonylaminobenzoyl)piperidine
85. 4-(4-methylsulfonylaminobenzoyl)-1-[2-(2-quinoxalinyl)ethyl]piperidine
86. 4-(4-methylsulfonylaminobenzoyl)-1-[2-(7-theophylinyl)ethyl]piperidine
87. 1-(9-fluorenyl)-4-(4-methylsulfonylaminobenzoyl)-piperidine 88. 1-ethyl-4-(4-methylsulfonylaminobenzoyl)piperidine
89. 1-n-butyl-4-(4-methylsulfonylaminobenzoyl)piperidine
90. 1-cyclohexylmethyl-4-(4-methylsulfonylaminobenzoyl)piperidine
91. 1-(2-methyl-2-propenyl)-4-(4-methylsulfonylaminobenzoyl)piperidine
92. 1-(ethoxycarbonylmethyl)-4-(4-methylsulfonylaminobenzoyl)piperidine
93. 1-cyano-4-(4-methylsulfonylaminobenzoyl)piperidine
94. 1-cyanomethyl-4-(4-methylsulfonylaminobenzoyl)piperidine
95. 1-(3-cyanopropyl)-4-(4-methylsulfonylaminobenzoyl)piperidine
96. 1-[2-(N',N'-diethylamino)ethyl]-4-(4-methylsulfonylaminobenzoyl)piperidine
97. 4-(4-methylsulfonylaminobenzoyl)-1-[2-(1-pyrrolidinyl)ethyl]piperidine
98. 4-(4-methylsulfonylaminobenzoyl)-1-[2-(1-piperidinyl)ethyl]piperidine
99. 4-(4-methylsulfonylaminobenzoyl)-1-[2-(4-morpholinyl)ethyl]piperidine
100. 4-(4-methylsulfonylaminobenzoyl)-1-[3-(1-piperidinyl)propyl]piperidine
101. 1-[3-(4-pyridyl)propyl]-4-[4-(p-toluenesulfonylamino)benzoyl]piperidine
102. 1-[2-(6-methyl-2-pyridyl)ethyl]-4-[4-(p-toluenesulfonylamino)benzoyl]piperidine
103. 4-(4-methylsulfonylaminobenzyl)-1-[2-(3-pyridyl)ethyl]piperidine
104. 1-[2-(3,4-dimethoxyphenyl)ethyl]-4-(4-methylsulfonylaminobenzyl)piperidine
105. 3-(4-methylsulfonylaminobenzoyl)-1-[2-(3-pyridyl)ethyl]piperidine
106. 1-[2-(6-methyl-2-pyridyl)ethyl]-3-(4-methylsulfonylaminobenzoyl)piperidine
107. 3-(4-methylsulfonylaminobenzoyl)-1-[2-(3-pyridyl)ethyl]pyrrolidine
108. 1-[2-(6-methyl-2-pyridyl)ethyl]-3-(4-methylsulfonylaminobenzoyl)pyrrolidine
109. 1-[2-(3,4-dimethoxyphenyl)ethyl]-3-(4-methylsulfonylaminobenzoyl)piperidine
110. 1-ethyl-4-(N-ethyl-4-methylsulfonylaminobenzoyl)piperidine
111. 1-n-butyl-4-(N-n-butyl-4-methylsulfonylaminobenzoyl)piperidine
112. 1-cyclohexylmethyl-4-(N-cyclohexylmethyl-4-methylsulfonylaminobenzoyl)piperidine
113. 1-(2-methyl-2-propenyl)-4-[N-(2-methyl-2-propenyl)-4-methylsulfonylaminobenzoyl]piperidine
114. 4-(4-methylsulfonylaminobenzoyl)-1-(2-(4-methylsulfonylaminophenyl)-2-oxoethyl)piperidine The piperidine derivatives obtained according to the present invention prolong the refractory period by specifically prolonging the action potential duration to prevent arrhythmia without exerting any influence on the myocardiac conduction velocity. These derivatives are antiarrhythmic agents of Class III of the above-mentioned Vaughan-Williams classification.

The following experimental examples will further illustrate the effects of the compounds of the present invention.

EXPERIMENTAL EXAMPLE 1

Effects on the Action Potential Duration in the Isolated Myocardium of Guinea-Pigs Right ventricular papillary muscles were isolated from male guinea-pigs of Hartley strain weighing 300 to 400 g and fixed at the bottom of an acrylic bath with pins. They were perfused with Tyrode solution kept at 37° C. and saturated with a mixture of 95% $O_2$ and 5% $CO_2$. The muscles were stimulated at 1 Hz with rectangular pulses of 1 msec duration and supramaximal voltage. Action potentials were recorded using conventional glass microelectrodes filled with 3M KCl. The duration of the action potential and the maximum velocity of the upstroke of the action potential (Vmax) were determined. Each of the test compounds was included in Tyrode solution at $10^{-6}$ or $10^{-5}$M and perfused. The effects of the $10^{-6}$M solution was observed for the first 10 min, then those of the $10^{-5}$M solution were observed for another 10 min.

The results are shown in Table 1. The test compounds shown in Example 1 were as follows. Sotalol, a beta-adrenoceptor antagonist was employed as the reference drug because this compound is known to prolong the duration of the myocardial action potential.

TEST COMPOUND

Compound A: 1-benzyl-4-(4-methylsulfonylaminobenzoyl)piperidine hydrochloride

Compound B: 4-(4-methylsulfonylaminobenzoyl)-1-(2-phenylethyl)piperidine hydrochloride Compound C: 1-[2-(4-chlorophenyl)ethyl]-4-(4-methylsulfonylaminobenzoyl)piperidine hydrochloride Compound D: 1,4-di(4-methylsulfonylaminobenzoyl)piperidine hydrochloride Compound E: 1-[2-(3,4-dimethoxyphenyl)ethyl]-4-(4-methylsulfonylaminobenzoyl)piperidine hydrochloride Compound F: 4-(4-methylsulfonylaminobenzoyl)-1-[2-(2-thienyl)ethyl]piperidine methylsulfonate Compound G: 4-(4-methylsulfonylaminobenzoyl)-1-(4-pyridyl)methylpiperidine dihydrochloride Compound H: 4-(4-methylsulfonylaminobenzoyl)-1-[2-(2-pyridyl)ethyl]piperidine dihydrochloride Compound I: 4-(4-methylsulfonylaminobenzoyl)-1-[2-(3-pyridyl)ethyl]piperidine dihydrochloride Compound J: 4-(4-methylsulfonylaminobenzoyl)-1-[2-(4-pyridyl)ethyl]piperidine dihydrochloride, and Compound K: 4-(4-methylsulfonylaminobenzoyl)-1-nicotinoylpiperidine.

Compound L(28): 4-(4-methylsulfonylaminobenzoyl)-1-(2-quinolylmethyl)piperidine dihydrochloride Compound M(29): 4-(4-methylsulfonylaminobenzoyl)-1-(3-quinolylmethyl)piperidine dihydrochloride Compound N(7): 1-[2-(3-imidazol[1,2-a]pyridyl)-2-oxoethyl]-4-(4-methylsulfonylaminobenzoyl)piperidine dihydrochloride Compound O(30): 1-(1-imidazo[1,2-a]pyridylmethyl)-4-(4-methylsulfonylaminobenzoyl)piperidine dihydrochloride Compound P(12): 1-ethyl-4-(4-methylsulfonylaminobenzoyl)piperidine hydrochloride Compound Q(31): 1-(6-imidazo[1,2-a]pyridylmethyl)-4-(4-methylsulfonylaminobenzoyl)piperidine dihydrochloride Compound R: 4-(4-methylsulfonylaminobenzoyl)-1-(3-(4-pyridyl)propyl)piperidine dihydrochloride Compound S: 1-(2-(6-methyl-2-pyridyl)ethyl)-4-(4-methylsulfonylaminobenzoyl)piperidine dihydrochloride

TABLE 1

| Test Compound | $10^{-6}$ M APD$_{90}$ prolongation (%) | $10^{-6}$ M $\dot{V}_{max}$ inhibition (%) | $10^{-5}$ M APD$_{90}$ prolongation (%) | $10^{-5}$ M $\dot{V}_{max}$ inhibition (%) |
|---|---|---|---|---|
| A | 0 | 0 | 7 | 0 |
| B | 26 | 0 | 34 | 19 |
| C | 7 | 0 | 15 | 0 |
| D | 3 | 0 | 10 | 0 |
| E | 12 | 0 | 14 | 0 |
| F | 8 | 0 | 11 | 0 |
| G | 18 | 0 | 33 | 0 |
| H | 2 | 0 | 5 | 0 |
| I | 10 | 0 | 17 | 0 |
| J | 4 | 0 | 10 | 0 |
| K | 9 | 0 | 24 | 14 |
| R | 18 | 0 | 27 | 0 |
| S | 20 | 0 | 30 | 0 |
| Sotalol | 0 | 0 | 7 | 0 |
| L | 18 | 0 | 26 | 2 |
| M | 3 | 0 | 5 | 0 |
| N | 8 | 0 | 8 | 0 |
| O | 6 | 0 | 12 | 5 |
| P | 7 | 0 | 23 | 2 |
| Q | 4 | 0 | 23 | 0 |

EXPERIMENTAL EXAMPLE 2

Effects on QTc-interval of ECG in Anesthetized Dogs

Mongrel dogs were anesthetized with enflurane. The chest was opened at the fifth intercosta and the pericardium was incised to expose the left ventricle. A monopolar electrode fixed on an acrylic plate was sutured to a ventricular surface of the region where the left anterior descending branch of the coronary artery was dominant. The electrocardiogram was recorded from the surface of the left ventricle through the electrode. Test compounds were injected through a catheter inserted into a forearm vein.

Compound B caused a 51% prolongation of QTc-interval (i.e. from 435 to 665 msec) at 0.1 mg/kg. Compound G produced 17, 27 and 35% prolongation of QTc-interval at 0.1, 0.3 and 1 mg/kg, respectively. When the test compound J was injected at 0.1 and 0.3 mg/kg, QTc-interval was prolonged by 21 and 42%, respectively.

When the test compound L was used, the QTc prolongation of 31% with 0.1 mg/kg and 56% with 0.3 mg/kg thereof were recognized. When the test compound M was used, the QTc prolongation of 7% with 0.1 mg/kg, 13% with 0.3 mg/kg and 21% with 1.0 mg/kg thereof were recognized. When the test compound P was used, the QTc prolongation of 7% with 0.1 mg/kg and 14% with 0.3 mg/kg thereof were recognized. The administrations of 0.03 mg/kg and 0.1 mg/kg of the compound R were found to provide 13% prolongation and 21% prolongation of QTc-interval, respectively. As to the compound S, the administrations of 0.01 mg/kg and 0.03 mg/kg were found to provide 30% prolongation and 42%. With 1.0 mg/kg of Sotanol used as a control, 12% prolongation was observed.

EXPERIMENTAL EXAMPLE 3

Acute Toxicity in Mice

Male ddy mice weighing 20 to 30 g were used for the acute toxicity test. LD50 values were calculated by the up-and-down method. The compounds G, J, M, N, O, R and sotalol were dissolved in saline to obtain 16 mg/ml stock solution. Administration of 0.1 ml of the solution to 10 g body weight of the animal corresponds to 160 mg/kg of the sample. The compounds B, F, L and S (the free body) were each dissolved in 20% polyethyleneglycol to obtain stock solutions having a concentration of 8 mg/ml. The dose to be administered was determined on the basis of the volume of the stock solution. The solutions were injected into a tail vein by means of a 1-ml tuberculin syringe. The judgement of survival or death was made 30 min after each injection. The results are shown in Table 2.

TABLE 2

| Compound | LD$_{50}$(iv) mg/kg |
|---|---|
| B | 100 |
| F | 112 |
| G | 108 |
| J | 195 |
| L | 112 |
| M | 112 |
| N | 224 |
| O | 302 |
| R | 138 |
| S | 112 |
| Sotalol | 113 |

It is apparent from the above Experimental Examples 1 and 2 that the compounds of the present invention have the pharmacological properties required for the antiarrhythmic agents of Class III, namely the prolongation of the myocardial action potential in vitro without a significant depression of the $\dot{V}$max and the prolongation of QTc-interval in anesthetized dogs. Moreover, their effects were much more potent than the reference drug, sotalol.

It is expected that the compounds of the present invention are effective in treating and preventing all types of arrhythmias including ventricular and atrial (supraventricular) arrhythmias. The compounds of the present invention are especially expected to control recurrent arrhythmias and prevent sudden death due to the ventricular fibrillation.

The compounds of the present invention can be used either orally or parenterally (intramuscular, subcutaneous or intravenous injection). The dose is not particularly limited, since it varies depending on the type of the arrhythmia, symptoms, age, condition and body weight of the patient. In case when used in combination with other drugs or treatments, it also depends on the kind, frequency and intended effects of the drug or the treatment. The usual oral dose for the adults dose is estimated to be 1 to 100 mg/day, preferably 5 to 50 mg/day and particularly 5 to 15 mg/day. The administration will be made once a day or more. In the case of injection, the dose is estimated to be 0.01 to 1 mg/kg, preferably 0.03 to 0.1 mg/kg.

The compound of the present invention can be given in the form of, for example, powders, finely divided particles, granules, tablets, capsules suppositories and injections. The preparations are produced by an ordinary process by using an ordinary carrier.

More particularly, for example, an oral solid preparation is produced by adding an excipient and, if necessary, a binder, disintegrator, lubricant, colorant, corrigent, etc. to the active ingredient and the mixture is shaped into tablets, coated tablets, granules, powder, capsules, etc.

Examples of the excipients include lactose, corn starch, white sugar, glucose, sorbitol, crystalline cellulose and silicon dioxide. Examples of the binders include polyvinyl alcohol, polyvinyl ethers, ethylcellulose, methylcellulose, acacia gum, tragacanth, gelatin, shellac, hydroxypropylcellulose, hydroxypropylstarch and polyvinylpyrrolidone. Examples of the disintegrators include starch, agar, gelatin powder, crystalline cellulose, calcium carbonate, sodium hydrogencarbonate, calcium citrate, dextrin and pectin. Examples of the lubricants include magnesium stearate, talc, polyethylene glycol, silica and hardened vegetable oils. The colorants are those acceptable as additives for medicines. Examples of the corrigents include cocoa powder, menthol, aromatic acids, peppermint oil, borneol and cinnamon powder. As a matter of course, these tablets and granules may be coated suitably with sugar, gelatin or the like.

In the production of the injection, a pH adjustor, buffer, stabilizer, solubilizer, etc. are added, if necessary, to the active ingredient and an intravenous injection is produced by an ordinary method.

The following examples will further illustrate the present invention, which by no means limit the present invention.

The final step in the production of the intended compound of the present invention will be shown in the following examples and the production of the starting materials used in the examples will be shown in the following referential examples.

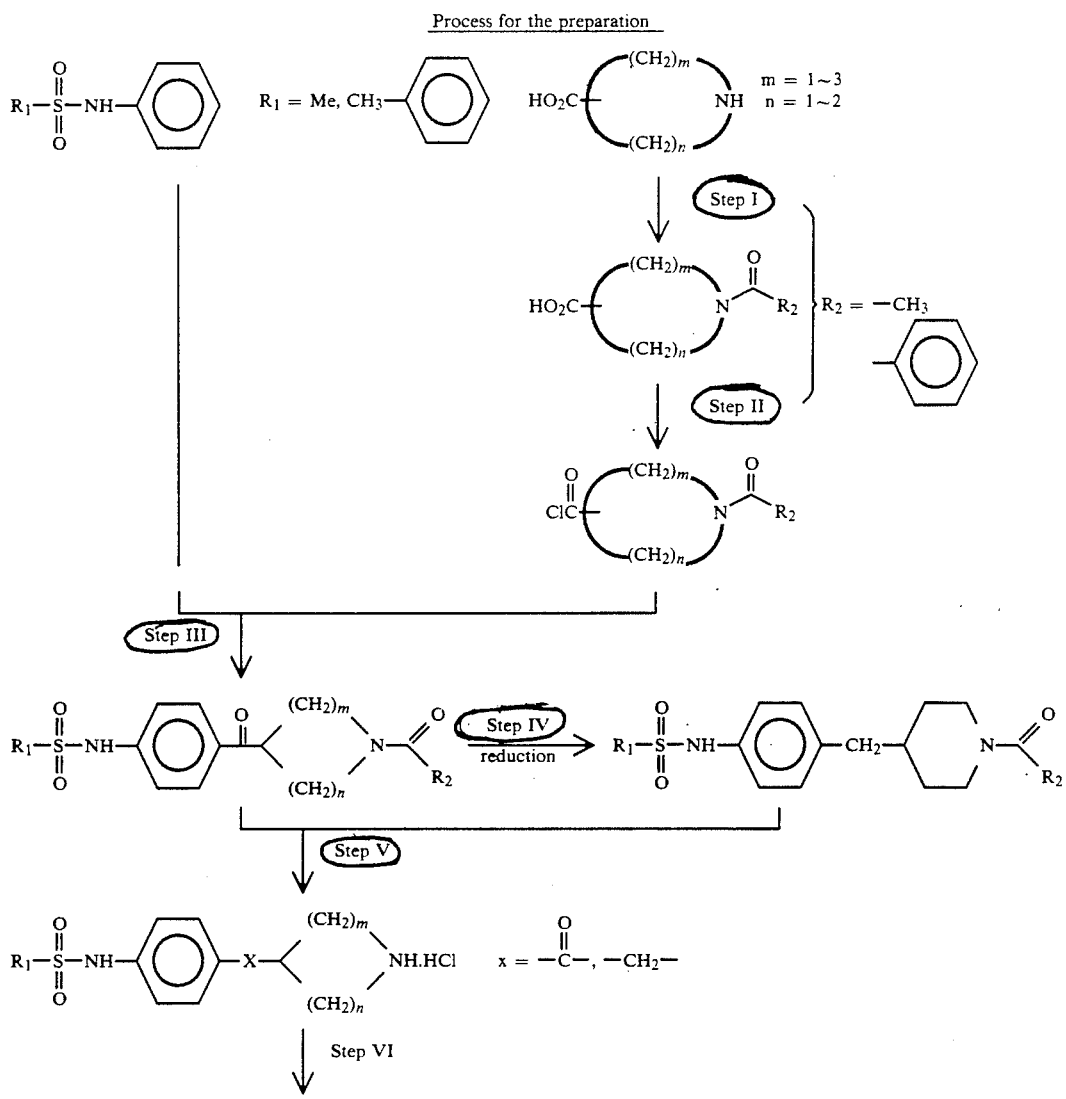

-continued

Process for the preparation

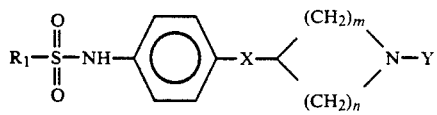

STEP I

Referential Example 1

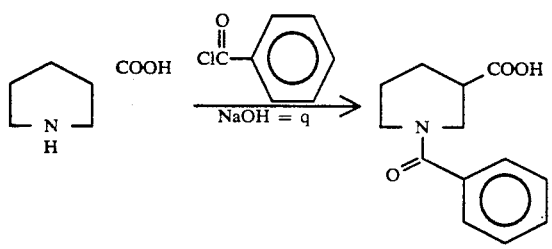

Preparation of (±)-N-benzoylnipecotic acid 20.0 g (155 mmol) of (±)-nipecotic acid was dissolved in 33 ml of a 20% aqueous sodium hydroxide solution. 23.84 g of benzoyl chloride was added dropwise thereto at such a rate that the reaction temperature would not exceed 20° C. Then 60 ml of a 20% aqueous sodium hydroxide solution was added dropwise thereto and the obtained mixture was stirred at 0° C. for 1 h, acidified with concentrated hydrochloric acid and extracted with dichloromethane. The organic layer was washed with water and a saturated aqueous common salt solution, dried over magnesium sulfate and concentrated. The solid residue was recrystallized from ethanol to obtain 18.0 g (yield: 40%) of the intended compound in the form of white crystals.

Melting point: 187° to 188° C.

NMR (90° C., DMSO-$d_6$) δ 1.3–2.2 (4H, m) 2.2–4.4 (5H, m) 7.42 (5H, S) 12.0–12.6 (1H, br).

The same procedure as above was repeated except that (±)-nipecotic acid was replaced with (±)-β-proline to obtain the following compound:

(±)-N-benzoyl-β-proline

Melting point: 111° to 113° C.

NMR (90 MHz, CDCl$_3$) δ 2.18 (2H, q-like, J=7 Hz) 2.8–3.3 (1H, m) 3.35–4.00 (4H, m) 7.36 (5H, m).

STEP II

Referential Example 2

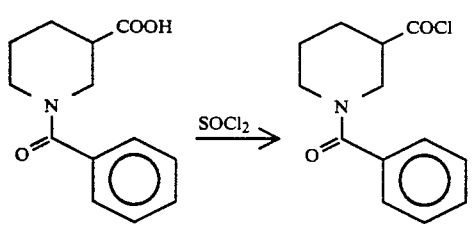

Preparation of (±)-N-benzoylnipecotoyl chloride 10.0 g (42.9 mmol) of (±)-N-benzoylnipecotic acid was dissolved in 15 ml of thionyl chloride. Several drops of dimethylformamide were added to the solution and the mixture was stirred at room temperature for 2 h. Excess thionyl chloride was distilled off under reduced pressure to obtain the intended compound in the form of a colorless oil almost quantitatively.

The same procedure as above was repeated except that (±)-N-benzoylnipecotic acid was replaced with (±)-N-benzoyl-β-proline to obtain the following compound:

(±)-N-Benzoyl-β-prolyl chloride

The acid chloride thus obtained in Referential Example 2 was used in the subsequent reaction (Referential Example 3) without purification.

STEP III

Referential Example 3

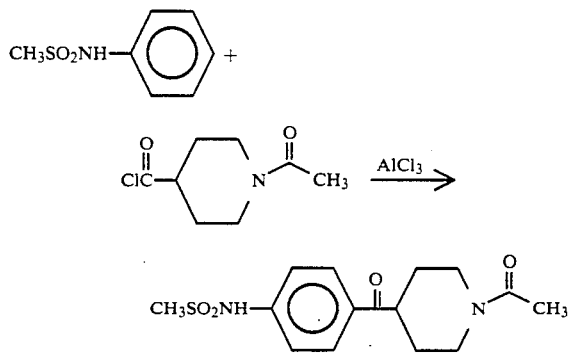

1-Acetyl-4-(4-methylsulfonylaminobenzoyl)piperidine 14.40 g (0.108 mol) of aluminum chloride was suspended in 25 ml of methylene chloride. 5.50 g (0.029 mol) of 1-acetylisonipecotoyl chloride and 5.00 g (0.029 mol) of methanesulfonanilide were added to the suspension under stirring and the obtained mixture was refluxed for 2 h. After cooling, the liquid reaction mixture was poured into 100 ml of ice/water and the mixture was stirred violently. Crystals thus formed were recovered by filtration and dried to obtain 7.22 g of the intended compound.

Melting point: 210° to 211.5° C.

NMR (90 MHz, DMSO-$d_6$) δ 1.20–2.00 (4H, m), 2.00 (3H, s), 2.60–4.00 (4H, m), 3.10 (3H, s), 4.36 (1H, broad), 7.28 (2H, d, J=8 Hz), 10.34 (1H, s, $D_2O$ exchange).

The same procedure as above was repeated except that methanesulfonamilide was replaced with p-toluenesulfonanilide or 1-acetylisonipecotoyl chloride was replaced with (±)-N-benzoylnipecotoyl chloride or (±)-N-benzoyl-β-prolyl chloride prepared in Referential Example 2 to obtain the following compounds:

1-acetyl-4-(4-ethylsulfonylaminobenzoyl)piperidine

NMR (90 MHz, CDCl$_3$) δ: 1.35 (3H, t, J=7 Hz), 1.5~2.10 (4H, m), 2.11 (3H, s), 2.65~3.70 (3H, m), 3.16 (2H, q, J=7 Hz), 3.88 (1H, brd, J=12 Hz), 4.51 (1H, br, J=12 Hz), 7.28 (2H, d, J=8 Hz), 7.83 (2H, d, J=8 Hz), 8.60 (1H, brs, D₂O exchange).

1-acetyl-4-(2-hydroxy-4-methylsulfonylaminobenzoyl)-piperidine

NMR (90 MHz, CDcl₃) δ: 1.2~2.0 (4H, m), 1.99 (3H, s), 3.10 (3H, s), 4.16 (1H, brd, J=13 Hz), 6.62~6.80 (2H, m), 7.90 (1H, d, J=8 Hz), 10.34 (1H, s, D₂O exchange), 13.22 (1H, s, D₂O exchange).

1-acetyl-4-(2-methoxy-4-methylsulfonylaminobenzoyl)-piperidine

NMR (90 MHz, DMSO-d₆) δ: 1.2~2.0 (4H, m), 2.00 (3H, s), 3.12 (3H, s), 3.88 (3H, s), 6.86 (1H, dd, J=8.2 Hz), 6.96 (1H, d, J=2 Hz), 7.57 (1H, d, J=8 Hz), 10.34 (1H, s, D₂O exchange).

1-acetyl-4-(4-p-toluenesulfonylaminobenzoyl)piperidine

NMR (90 MHz, CDCl₃) δ 1.4-2.0 (4H, m) 2.14 (3H, s) 2.37 (3H, s) 2.5-3.6 (3H, m) 3.92 (1H, brd, J=14 Hz) 4.57 (1H, brd, J=14 Hz) 7.23 (4H, d, J=8 Hz) 7.75 (2H, d, J=8 Hz) 7.83 (2H, d, J=8 Hz) 8.80 (1H, br).

(±)-1-benzoyl-3-(4-methylsulfonylaminobenzoyl)-piperidine

NMR (90 MHz, DMSO-d₆) δ 1.5-2.2 (4H, m) 3.00 (3H, s) 7.24 (2H, m) 7.42 (5H, s) 7.88 (2H, m) etc.

(±)-1-benzoyl-3-(4-methylsulfonylaminobenzoyl)pyrrolidine

NMR (90 MHz, CDCl₃) δ 1.9-3.0 (3H, m) 3.01 (3H, s) 3.4-4.2 (4H, m) 7.34 (7H, m) 7.84 (2H, m).

Referential Example 4

1-Acetyl-N-methyl-4-(4-methylsulfonylaminobenzoyl)-piperidine 3.24 g (10.0 mmol) of 1-acetyl-4-(4-methylsulfonylaminobenzoyl)piperidine was added to a suspension of 0.29 g (12.0 mmol) of sodium hydride in 30 ml of dimethylformamide in a nitrogen atmosphere and the mixture was stirred at 60° C. for 20 min. 1.7 g (12.0 mmol) of methyl iodide was added to the liquid mixture and the obtained mixture was stirred at 60° C. for 1 h. 100 ml of chloroform was added thereto and the mixture was washed with water and saturated aqueous common salt solution. The chloroform layer was concentrated and the residual oil was subjected to column chromatography (chloroform:methanol=99:1) to concentrate the intended fraction. 2.0 g of the intended compound was obtained.

Melting point (°C.): 162 to 163.

NMR (90 MHz, CDCl₃) δ:1.5~2.1 (4H, m) 2.11 (3H, s), 2.95 (3H, s), 3.37 (3H, s), 3.92 (1H, br, J=13 Hz), 4.56 (1H, d, J=13 Hz), 7.50 (2H, d, J=8 Hz), 7.96 (2H, d, J=8 Hz).

STEP IV

Referential Example 5

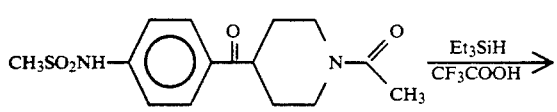

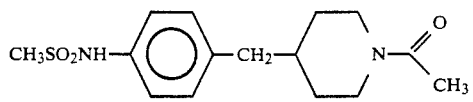

Preparation of 1-acetyl-4-(4-methylsulfonylaminobenzyl)piperidine 7.50 g (23.1 mmol) of 1-acetyl-4-(4-methylsulfonylaminobenzoyl)piperidine obtained in Referential Example 3 was dissolved in 110 ml of dichloroethane. 11.0 ml of triethylsilane and 17.8 ml of trifluoroacetic acid were added to the solution and the mixture was refluxed for 50 h. After cooling, a 20% aqueous sodium hydroxide solution was added thereto to neutralize the same. After extraction with dichloromethane, the organic layer was washed with water and a saturated aqueous common salt solution, dried over magnesium sulfate and concentrated. The obtained oily residue was purified according to silica gel column chromatography (chloroform:methanol=98:2) to obtain 3.30 g (yield: 46%) of the intended compound in the form of white crystals.

Melting point: 145° to 146° C.

NMR (90 MHz, CDCl₃) δ 1.4-2.0 (3H, m) 2.08 (3H, s) 2.2-3.1 (4H, m) 3.00 (3H, s) 3.78 (1H, brd, J=13 Hz) 4.56 (1H, brd, J=13 Hz) 7.12 (4H, m).

| Elementary analysis for C₁₅H₂₂N₂O₃S: | | | |
| --- | --- | --- | --- |
| | C | H | N |
| calculated (%) | 58.04 | 7.14 | 9.02 |
| found (%) | 57.64 | 6.93 | 9.00 |

STEP V, PART 1

Example 1

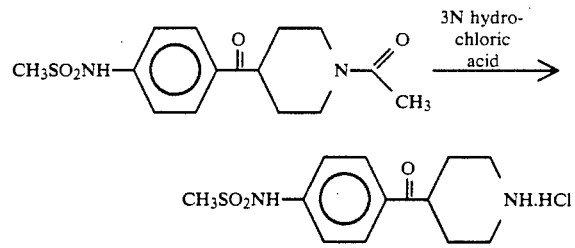

4-(4-Methylsulfonylaminobenzoyl)piperidine hydrochloride 43.4 g (0.142 mol) of 1-acetyl-4-(4-methylsulfonylaminobenzoyl)piperidine was suspended in 1 l of 3N hydrochloric acid and the suspension was stirred under reflux for 3 h. After completion of the reaction, the liquid reaction mixture was cooled and white crystals thus formed were filtered, washed with water and dried to obtain 37.8 g (yield: 84%) of the intended compound.

Melting point: >265° C. (decomp.).

NMR (90 MHz, DMSO-d₆) δ: 1.6-2.1 (4H, m), 3.12 (3H, s) 7.33 (2H, d, J=8 Hz), 8.01 (2H, d, J=8 Hz), 8.8-9.5 (2H, br, D₂O exchange), 10.46 (1H, s, D₂O exchange).

| Elementary analysis for $C_{13}H_{18}N_2O_3S\cdot HCl$: | | | |
|---|---|---|---|
| | C | H | N |
| calculated (%) | 48.98 | 6.01 | 8.79 |
| found (%) | 48.64 | 5.77 | 8.65 |

The same procedure as above was repeated except that the same starting materials as in the above referential examples were used to obtain the following compounds.

Example 2

4-(4-Ethylsulfonylaminobenzoyl)piperidine hydrochloride

Melting point (°C.): >220 (decomp.).
NMR (90 MHz, DMSO-d$_6$) δ: 1.22 (3H, t, 7 Hz), 1.62~2.1 (4H, m), 2.8~3.9 (4H, m), 3.21 (3H, q, J=7 Hz), 7.34 (2H, d, J=8 Hz), 8.01 (2H, d, J=8 Hz), 8.8~9.5 (2H, br), 10.38 (1H, s, D$_2$O exchange).

| Elementary analysis for $C_{14}H_{20}N_2O_3S\cdot HCl$: | | | |
|---|---|---|---|
| | C | H | N |
| calculated (%) | 50.52 | 6.06 | 8.42 |
| found (%) | 50.31 | 6.30 | 8.29 |

Example 3

4-(2-Hydroxy-4-methylsulfonylaminobenzoyl)piperidine hydrochloride

Melting point (°C.): >250.
NMR (90 MHz, DMSO-d$_6$) δ: 1.6~2.1 (4H, m), 3.10 (3H, s), 6.65~6.87 (2H, m), 7.89 (1H, d, J=8 Hz), 8.6~9.4 (2H, br, D$_2$O exchange), 10.40 (1H, s, D$_2$O exchange), 12.05 (1H, s, D$_2$O exchange).

| Elementary analysis for $C_{13}H_{18}N_2O_4S\cdot HCl$: | | | |
|---|---|---|---|
| | C | H | N |
| calculated (%) | 46.64 | 5.72 | 8.37 |
| found (%) | 46.71 | 5.97 | 8.30 |

Example 4

4-(2-Methoxy-4-methylsulfonylaminobenzoyl)piperidine hydrochloride

Melting point (°C.): >220 (decomp.).
NMR (90 MHz, DMSO-d$_6$) δ: 1.5~2.1 (4H, m), 3.12 (3H, s), 3.88 (3H, s), 6.86 (1H, dd, J=8, 2 Hz), 6.96 (1H, d, J=2 Hz), 7.58 (1H, d, J=8 Hz), 9.0 (2H, br, D$_2$O exchange), 10.32 (1H, s, D$_2$O exchange).

| Elementary analysis for $C_{14}H_2ON_2O_4S\ HCl$: | | | |
|---|---|---|---|
| | C | H | N |
| calculated (%) | 48.20 | 5.78 | 8.03 |
| found (%) | 48.32 | 5.93 | 7.81 |

The same procedure as above was repeated except that 1-acetyl-4-(4-methylsulfonylaminobenzoyl)piperidine was replaced with 1-acetyl-4-(4-p-toluenesulfonylaminobenzoyl)piperidine or 1-acetyl-4(4-methylsulfonylaminobenzyl)piperidine to obtain the following compounds:

Example 5

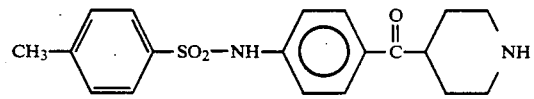

4-(4-p-toluenesulfonylaminobenzoyl)piperidine hydrochloride

Melting point: 240° to 242° C.
NMR (90 MHz, DMSO-d$_6$) δ 1.6–2.1 (4H, m) 2.5–3.8 (5H, m) 2.36 (3H, s) 7.24 (2H, d, J=8 Hz) 7.36 (2H, d, J=8 Hz) 7.76 (2H, d, J=8 Hz) 7.90 (2H, d, J=8 Hz) 9.0 (2H, br) 10.97 (1H, s).

| Elementary analysis for $C_{19}H_{22}N_2O_3S\cdot HCl\cdot H_2O$: | | | |
|---|---|---|---|
| | C | H | N |
| calculated (%) | 55.27 | 5.61 | 6.78 |
| found (%) | 55.25 | 5.68 | 6.85 |

Example 6

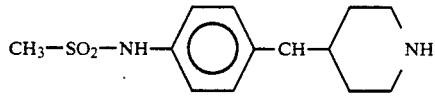

4-(4-Methylsulfonylaminobenzyl)piperidine hydrochloride

Melting point: 255° to 257° C.
NMR (90 MHz, DMSO-d$_6$) δ 1.2–2.0 (5H, m) 2.94 (3H, s) 7.14 (4H, s) 9.0 (2H, br) 9.67 (1H, s).

| Elementary analysis for $C_{13}H_{20}N_2O_2S\cdot HCl$: | | | |
|---|---|---|---|
| | C | H | N |
| calculated (%) | 51.22 | 6.94 | 9.19 |
| found (%) | 51.26 | 6.86 | 9.16 |

STEP V, PART 2

Example 7

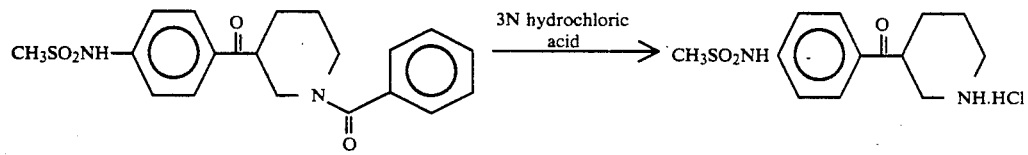

(±)-3-(4-Methylsulfonylaminobenzoyl)piperidine hydrochloride 5.70 g (14.8 mmol) of (±)-1-benzoyl-3-(4-methylsulfonylaminobenzoyl)piperidine obtained in Referential Example 3 was dissolved in a mixture of 120 ml of 5N hydrochloric acid and 80 ml of methanol and the obtained solution was refluxed for 8 h. The reaction solution was concentrated and the obtained solid residue was recrystallized from ethanol to obtain 2.61 g (yield: 55%) of the intended compound in the form of white crystals.

Melting point: 235° to 237° C.

NMR (90 MHz, DMSO-d$_6$) δ 1.4–2.2 (4H, m) 2.6–4.1 (5H, m) 3.11 (3H, s) 7.35 (2H, d, J=8 Hz) 7.98 (2H, d, J=8 Hz) 8.0–8.5 (2H, br) 10.48 (1H, brs).

| Elementary analysis for C$_{13}$H$_{18}$N$_2$O$_3$S.HCl: | | | |
|---|---|---|---|
| | C | H | N |
| calculated (%) | 48.98 | 6.01 | 8.79 |
| found (%) | 48.86 | 5.87 | 8.77 |

Example 8

The same procedure as in Example 7 was followed except that (±)-1-benzoyl-3-(4-methylsulfonylaminobenzoyl)piperidine was replaced with (±)-1-benzoyl-3-(4-methylsulfonylaminobenzoyl)pyrrolidine to obtain the following compound:

(±)-3-(4-Methylsulfonylaminobenzoyl)pyrrolidine hydrochloride

Melting point: 198° to 200° C.

NMR (90 MHz, DMSO-d$_6$) δ 1.7–2.5 (2H, m) 3.0–3.8 (4H, m) 3.14 (3H, s) 4.20 (1H, q-like, J=7 Hz) 7.36 (2H, d, J=8 Hz) 8.01 (2H, d, J=8 Hz) 9.5 (2H, br) 10.26 (1H, s).

| Elementary analysis for C$_{12}$H$_{16}$N$_2$O$_3$S.HCl: | | | |
|---|---|---|---|
| | C | H | N |
| calculated (%) | 47.29 | 5.62 | 9.19 |
| found (%) | 47.17 | 5.49 | 9.11 |

Example 9

N-Methyl-4-(4-methylsulfonylaminobenzoyl)piperidine hydrochloride 1.43 g (yield: 90%) of the intended compound was obtained from 1.90 g of 1-acetyl-N-methyl-4-(4-methylsulfonylaminobenzoyl)piperidine prepared in Referential Example 4.

Melting point (°C.): 254 to 255.

NMR (90 MHz, DMSO-d$_6$) δ: 1.5~2.1 (4H, m), 3.04 (3H, s), 3.32 (3H, s), 7.57 (2H, d, J=8H2), 8.06 (2H, d, J=8H2), 8.8–9.6 (2H, br, D$_2$O exchange).

| Elementary analysis for C$_{14}$H$_{20}$N$_2$SO$_3$.HCl: | | | |
|---|---|---|---|
| | C | H | N |
| calculated (%) | 50.50 | 6.37 | 8.42 |
| found (%) | 50.43 | 6.42 | 8.39 |

Example 10

4-(4-Methylsulfonylaminobenzoyl)-1-(4-pyridylmethyl)piperidine dihydrochloride 1.13 g (18.8 mmol) of sodium methoxide was added to a suspension of 3.0 g (9.4 mmol) of 4-(4-methylsulfonylaminobenzoyl)piperidine hydrochloride and 1.55 g (9.4 mmol) of 4-chloromethylpyridine hydrochloride in 90 ml of acetonitrile. The mixture was stirred at room temperature for 10 min. 2.88 g of potassium carbonate was added to the mixture and the obtained mixture was refluxed for 3 h. After cooling, the liquid reaction mixture was filtered and the filtrate was concentrated, while the residue was purified according to silica gel chromatography (chloroform:methanol=95:5). The product was converted into its hydrochloride with ethanolic hydrogen chloride and recrystallized from methanol/isopropanol to obtain 1.4 g of the intended compound:

Melting point: ~207° C. (decomp.).

NMR (400 MHz, DMSO-d$_6$) δ: 1.85~2.30 (4H, m), 3.11 (3H, s), 4.53 (2H, s), 7.31 (2H, d, J=8.8 Hz), 7.98 (2H, d, J=8.8 Hz), 8.17 (2H, d, J=4.9 Hz), 8.92 (2H, d, J=5.9 Hz), 10.41 (1H, s, D$_2$O exchange), 11.6~12.0 (1H, brs, D$_2$O exchange).

| Elementary analysis for C$_{19}$H$_{23}$N$_3$O$_3$S.2HCl: | | | |
|---|---|---|---|
| | C | H | N |
| calculated (%) | 51.12 | 5.64 | 9.41 |
| found (%) | 51.04 | 5.41 | 9.28 |

Example 11

4-(4-Methylsulfonylaminobenzoyl)-1-[2-(3-pyridyl)ethyl]piperidine dihydrochloride 35 g (0.101 mol) of 4-(4-methylsulfonylaminobenzoyl)piperidine hydrochloride and 55 g of potassium carbonate were suspended in 700 ml of dimethylformamide and the suspension was stirred at 40° C. for 20 min. 19.6 g (0.101 mol) of 3-(2-chloroethyl)pyridine hydrochloride and 6.0 g (0.036 mol) of potassium iodide were added to the suspension and the mixture was stirred at 90° C. for 3.5 h. The liquid reaction mixture was filtered and the filtrate was concentrated, while the residue was purified according to silica gel chromatography (chloroform:methanol=93:7). The purified product was converted into its hydrochloride with ethanolic hydrogen chloride and recrystallized from methanol/isopropanol to obtain 13.4 g of the intended compound.

Melting point (°C.): 200 to 203.

NMR (100 MHz, DMSO-d$_6$) δ: 1.8~2.3 (4H, m), 3.11 (3H, s), 7.32 (2H, d, J=8 Hz), 7.90~8.10 (3H, m), 8.50 (1H, dt, J=6, 2 Hz), 8.8 (1H, d, J=6 Hz), 8.93 (1H, d, J=2 Hz), 10.43 (1H, s, D$_2$O exchange), 10.90~11.40 (1H, br, D$_2$O exchange).

| Elementary analysis for C$_{20}$H$_{25}$N$_3$O$_3$S.2HCl | | | |
|---|---|---|---|
| | C | H | N |
| calculated (%) | 52.17 | 5.91 | 9.13 |
| found (%) | 52.00 | 5.86 | 8.83 |

Example 12

4-(4-Methylsulfonylaminobenzoyl)-1-[3-(4-pyridyl)-propyl]piperidine dihydrochloride 0.295 g (0.926 mmol) of 4-(4-methylsulfonylaminobenzoyl)piperidine hydrochloride and 0.380 g (4.52 mmol) of sodium hydrogencarbonate were suspended in 4 ml of dimethylformamide and the suspension was stirred at 85° C. for 40 min. 0.20 g (1.04 mmol) of 4-(3-chloropropyl)pyridine hydrochloride and 0.31 g (1.87 mmol) of potassium iodide were added to the suspension and the mixture was stirred at 85° C. for 1.5 h. The liquid reaction mixture was filtered and the filtrate was concentrated. The obtained residue was purified according to silica gel column chromatography (chloroform:methanol:aqueous ammonia=96:4:0.4). The purified product was converted into its hydrochloride with ethanolic hydrogen chloride and recrystallized from ethanol to obtain 0.288 g (66%) of the intended compound.

Melting point: 230° C. (decomp.)

NMR (100 MHz, DMSO-$d_6$) δ 1.8–2.4 (6H, m) 3.10 (3H, s) 7.30 (2H, d, J=8 Hz) 7.95 (2H, d, J=8 Hz) 7.97 (2H, d, J=6 Hz) 8.83 (2H, d, J=6 Hz) 10.44 (1H, brs, D$_2$O exchange) 10.9–11.4 (1H, br, D$_2$O exchange).

| Elementary analysis for $C_{21}H_{27}N_3O_3S.2HCl$: | | | |
|---|---|---|---|
| | C | H | N |
| calculated (%) | 53.16 | 6.16 | 8.86 |
| found (%) | 52.95 | 6.10 | 8.73 |

Example 13

1-[2-(6-Methyl-2-pyridyl)ethyl]-4-(4-methylsulfonylaminobenzoyl)piperidine dihydrochloride 0.254 g (0.797 mmol) of 4-(4-methylsulfonylaminobenzoyl)piperidine hydrochloride, 0.22 g (1.88 mmol) of 6-methyl-2-vinylpyridine and 0.15 g of sodium acetate were suspended in 3 ml of a mixture of methanol and water (1:1) and the suspension was refluxed for 2 h. The liquid reaction mixture was filtered and the filtrate was concentrated. The obtained residue was purified according to silica gel column chromatography (chloroform:methanol:aqueous ammonia=96:4:0.4). The purified product was converted into its hydrochloride with ethanolic hydrogen chloride and recrystallized from ethanol to obtain 0.285 g (yield: 81%) of the intended compound.

Melting point: 219° C. (decomp.).

NMR (90 MHz, DMSO-$d_6$) δ 1.6–2.4 (4H, m) 2.74 (3H, s) 3.12 (3H, s) 7.33 (2H, d, J=8 Hz) 7.70 (1H, d, J=7 Hz) 7.78 (1H, d, J=7 Hz) 8.02 (2H, d, J=8 Hz) 8.33 (1H, t, J=7 Hz) 10.47 (1H, s, D$_2$O exchange) 11.2 (1H, br, D$_2$O exchange).

| Elementary analysis for $C_{21}H_{27}N_3O_3S.2HCl$: | | | |
|---|---|---|---|
| | C | H | N |
| calculated (%) | 53.16 | 6.16 | 8.86 |
| found (%) | 52.94 | 6.16 | 8.73 |

Example 14

4-(4-Methylsulfonylaminobenzoyl)-1-[2-(4-pyridyl)ethyl]piperidine dihydrochloride (Another Process for Synthesizing the Compound of Example 29)

10.0 g (31.4 mmol) of 4-(4-methylsulfonylaminobenzoyl)piperidine hydrochloride was suspended in 20 ml of an aqueous solution of 1.32 g of sodium hydroxide and the suspension was stirred at room temperature for 1 h. The formed solid was filtered, washed with water and dried to obtain 8.28 g of crystals, which were suspended in a solution comprising 15 ml of water, 15 ml of methanol and 0.2 ml of acetic acid. 3.39 g of 4-vinylpyridine was added to the suspension and the mixture was refluxed for 10 h. After cooling, the formed crystals were filtered and converted into its hydrochloride with ethanolic hydrogen chloride to obtain 7.54 g of the intended compound.

The melting point and NMR signals of this compound coincided with those of the compound produced from 4-(4-methylsulfonylaminobenzoyl)piperidine hydrochloride and 4-(2-chloroethyl)pyridine in Example 29 in the same manner as in Example 13.

STEP VI, PART 1

Example 15

1-{2-(2-Imidazo[1,2-a]pyridyl)ethyl}-4-(4-methylsulfonylaminobenzoyl)piperidine

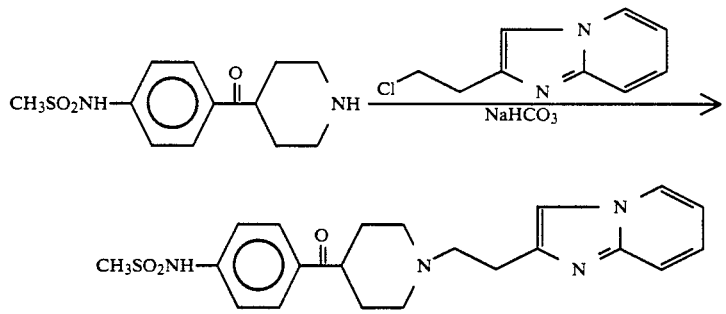

A mixture of 1.02 g (3.2 mmol) of 4-(4-methylsulfonylaminobenzoyl)piperidine hydrochloride, 1.34 g of sodium hydrogencarbonate and 10 ml of dimethylformamide was stirred at 80° C. for 1 h. 0.48 g of 2-(2-chloroethyl)imidazo[1,2-a]pyridine hydrochloride and 0.53 g of potassium iodide were added thereto and the mixture was stirred at 80° C. for 2 h. The mixture was filtered and the filtrate was concentrated to obtain a solid residue, which was then purified according to silica gel column chromatography (chloroform:methanol:aqueous ammonia=190:9:1). The fraction of the intended compound was concentrated to obtain a solid residue, which was then recrystallized from ethyl acetate to obtain 0.25 g (yield: 18%) of the intended compound.

Melting point: 190° to 191° C.

NMR (90 MHz, DMSO-d$_6$) δ 1.4–1.9 (4H, m) 2.18 (2H, m) 2.4–3.6 (7H, m) 3.10 (3H, s) 6.80 (1H, dt, J=5.2 Hz) 7.04–7.34 (4H, m) 7.72 (1H, s) 7.95 (2H, d, J=8 Hz) 8.45 (1H, d, J=7 Hz).

| Elementary analysis for C$_{22}$H$_{26}$N$_4$O$_3$S: | | | |
|---|---|---|---|
| | C | H | N |
| calculated (%) | 61.95 | 6.14 | 13.14 |
| found (%) | 61.92 | 6.10 | 12.92 |

Example 16

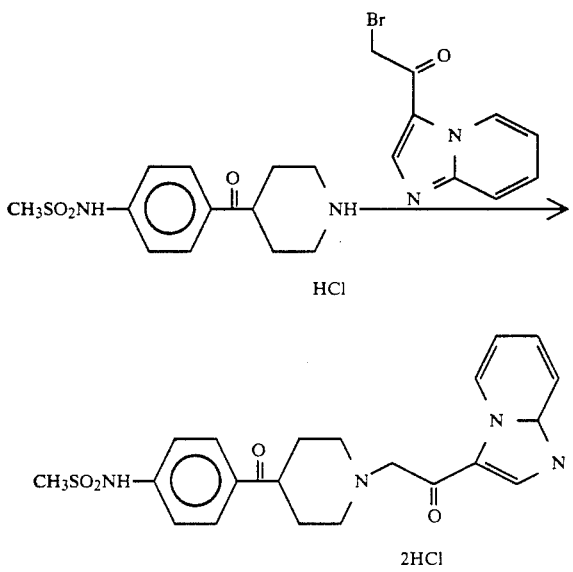

1-[2-(3-Imidazo[1,2-a]pyridyl)-1-oxoethyl]-4-(4-methylsulfonylaminobenzoyl)piperidine dihydrochloride i) 22.1 g of 3-acetylimidazo[1,2-a]pyridine was dissolved in 220 ml of acetic acid. 35.1 ml of a 30% hydrogen bromide/acetic acid solution was added dropwise to the solution at 0° C. Then 28.6 g of bromine was added dropwise thereto at 40° C. The mixture was stirred at 40° C. for 2 h and crystals thus formed were filtered. The crystals were dissolved in 100 ml of water. The solution was made alkaline with an excess of an aqueous sodium hydrogencarbonate solution and then extracted with ethyl acetate. The organic layer was concentrated and the obtained brown solid was purified according to silica gel column chromatography (eluted with ethyl acetate) to obtain 13.5 g (yield: 40%) of 3-bromoacetylimidazo[1,2-a]pyridine (yield: 40%) in the form of yellow crystals. ii) A suspension comprising 1.91 g (6.0 mmol) of 4-(4-methylsulfonylaminobenzoyl)-piperidine hydrochloride, 3.0 g of potassium carbonate and 40 ml of dimethylformamide was stirred at 80° C. for 1 h. After cooling to room temperature, 1.99 g of 3-bromoacetylimidazo[1,2-a]pyridine prepared in the above step i) was added thereto and the mixture was stirred at room temperature for 6 h. The reaction mixture was filtered and the filtrate was concentrated to obtain a solid residue, which was then purified according to silica gel column chromatography (chloroform:methanol=96:4). The purified product was converted into its dihydrochloride with ethanolic hydrogen chloride and recrystallized from methanol/acetone to obtain 1.75 g (yield: 58%) of the intended compound.

Melting point: 176° to 178° C.

NMR (400 MHz, DMSO-d$_6$) δ 1.95–2.10 (4H, m) 3.12 (3H, s) 3.33 (2H, m) 3.48–3.90 (3H, m) 4.96 (2H, s) 7.34 (2H, d, J=8.8 Hz) 7.51 (1H, t, J=7.1 Hz) 7.89 (1H, dd, J=7.8, 7.3 Hz) 8.02 (2H, d, J=8.8 Hz) 9.01 (1H, s) 9.54 (1H, d, J=6.8 Hz) 10.50 (1H, s, D$_2$O exchange) 10.72 (1H, br, D$_2$O exchange).

| Elementary analysis for C$_{22}$H$_{24}$N$_4$O$_4$S.2HCl.1.2H$_2$O: | | | |
|---|---|---|---|
| | C | H | N |
| calculated (%) | 49.39 | 5.35 | 10.47 |
| found (%) | 49.46 | 5.09 | 10.41 |

STEP VI, PART 3

Example 17

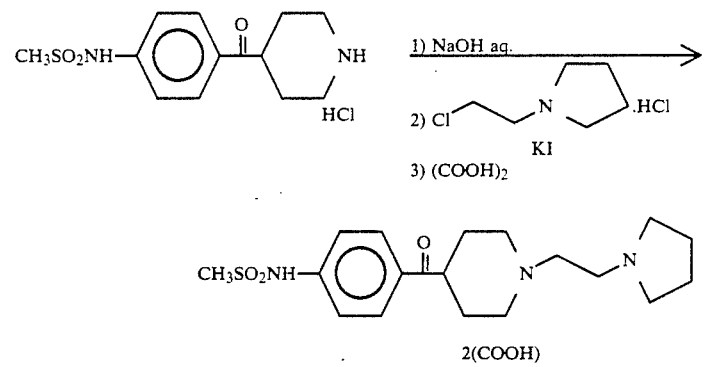

4-(4-Methylsulfonylaminobenzoyl)-1-[2-(1-pyrrolidinyl)ethyl]piperidine dioxalate 10.0 g (31.4 mmol) of 4-(4-methylsulfonylaminobenzoyl)piperidine hydrochloride was suspended in 20 ml of an aqueous solution of 1.32 g of sodium hydroxide and the suspension was stirred at room temperature for 1 h. The formed crystals were filtered, washed with water and dried to obtain 8.28 g of 4-(4-methylsulfonylaminobenzoyl)piperidine in free form. A mixture of 2.0 g (7.09 mmol) of the obtained crystals, 1.57 g of chloroethylpyrrolidine hydrochloride, 2.35 g of potassium iodide and 40 ml of dimethylformamide was stirred at 80° C. for 3 h. The reaction mixture was filtered and the filtrate was concentrated to obtain a solid residue, which was then purified according to silica gel column chromatography (chloroform:methanol:aqueous ammonia=90:9:1). 0.68 g of the purified product was converted into its dioxalate with 0.32 g of oxalic acid in ethanol. After recrystallization from methanol//ethanol, 0.40 g (yield: 10%) of the intended compound was obtained.

Melting point: 214° to 216° C.

NMR (90 MHz, DMSO-d$_6$) δ 1.4–2.3 (8H, m) 2.4–3.6 (13H, m) 3.08 (3H, s) 7.21 (2H, d, J=8 Hz) 7.88 (2H, d, J=8 Hz).

Elementary analysis for C$_{19}$H$_{29}$N$_2$O$_3$S.2(CCOH)$_2$:

|  | C | H | N |
|---|---|---|---|
| calculated (%) | 49.37 | 5.94 | 7.51 |
| found (%) | 49.40 | 5.85 | 7.37 |

STEP VI, PART 4

Example 18

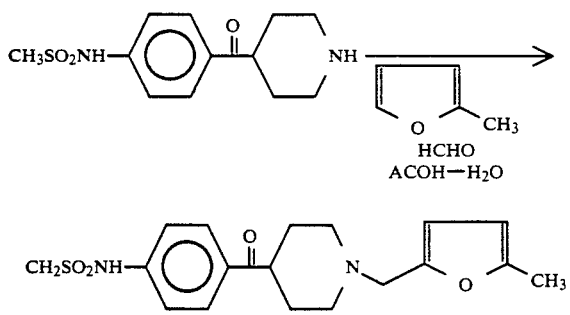

1-(5-Methyl-2-furanyl)methyl-4-(4-methylsulfonylaminobenzoyl)piperidine 1.88 ml of formalin and 1.07 g of methylfuran were added to a mixture of 4.43 g (15.7 mmol) of 4-(4-methylsulfonylaminobenzoyl)piperidine in free form obtained in Example 17, 1.57 ml of glacial acetic acid and 10 ml of water and the obtained mixture was stirred at 90° C. for 2 h. After cooling, the mixture was neutralized with a 20% aqueous sodium hydroxide solution and extracted with dichloromethane. The organic layer was washed with water and a saturated aqueous common salt solution, dried over magnesium sulfate and concentrated. The solid residue was recrystallized from ethanol/methanol to obtain 4.16 g (yield: 70%) of the intended compound.

Melting point: 181° to 182° C.

NMR (90 MHz, DMSO-d$_6$) δ 1.3–1.9 (4H, m) 1.9–2.3 (2H, m) 2.23 (3H, d, J=1 Hz) 2.6–3.4 (3H, m) 3.10 (3H, s) 3.43 (2H, s) 5.97 (1H, m) 6.13 (1H, d, J=3 Hz) 7.28 (2H, d, J=8 Hz) 7.94 (2H, d, J=8 Hz).

| Elementary analysis for C$_{19}$H$_{24}$N$_2$O$_4$S: | | | |
|---|---|---|---|
|  | C | H | N |
| calculated (%) | 60.62 | 6.43 | 7.44 |
| found (%) | 60.43 | 6.46 | 7.44 |

STEP VI, PART 5

Example 19

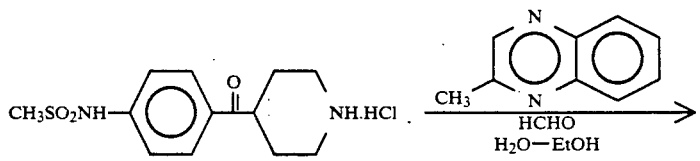

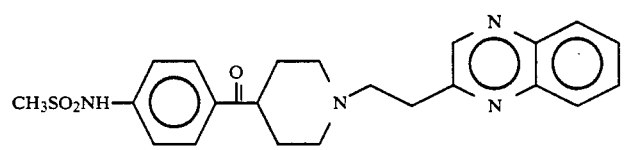

4-(4-Methylsulfonylaminobenzoyl)-1-[2-(2-quinoxalinyl)ethyl]piperidine 5.0 g (15.7 mmol) of 4-(4-methylsulfonylaminobenzoyl)piperidine hydrochloride was suspended in 5 ml of ethanol. 2.49 g of 2-methylquinoxaline and 7.0 ml of formalin were added to the suspension and the mixture was stirred at 90° C. for 1 h. After cooling, the mixture was neutralized with a 20% aqueous sodium hydroxide solution and the formed crystals were recrystallized from ethyl acetate to obtain 0.32 g (yield: 5%) of the intended compound.

Melting point: 156° to 157° C.

NMR (90 MHz, DMSO-d$_6$) δ 1.4–2.0 (4H, m) 2.0–2.4 (2H, m) 2.6–3.5 (7H, m) 3.13 (3H, s) 7.31 (2H, d, J=8 Hz) 7.73–8.15 (6H, m) 8.91 (1H, s).

| Elementary analysis for C$_{23}$H$_{26}$N$_4$O$_3$S: | | | |
|---|---|---|---|
|  | C | H | N |
| calculated (%) | 62.99 | 5.98 | 12.78 |
| found (%) | 62.83 | 5.95 | 12.61 |

STEP VI, PART 6

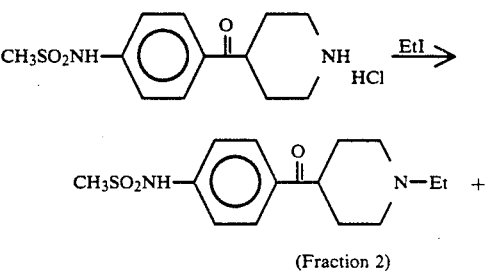

(Fraction 2)

-continued

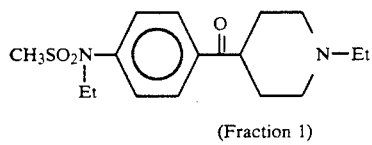

(Fraction 1)

Example 20 and 21

1-Ethyl-4-(4-methylsulfonylaminobenzoyl)piperidine
and
1-ethyl-4-(N-ethyl-4-methylsulfonylaminobenzoyl)-piperidine A suspension comprising 2.54 g (7.97 mmol) of 4-(4-methylsulfonylaminobenzoyl)piperidine hydrochloride, 5.0 g of potassium carbonate and 40 ml of dimethylformamide was stirred at 80° C. for 1 h. 1.3 g (8.3 mmol) of ethyl iodide was added thereto and the mixture was stirred at 80° C. for 12 h. The mixture was filtered and the filtrate was concentrated to obtain a solid residue, which was then purified according to silica gel column chromatography (chloroform:methanol:aqueous ammonia=190:9:1). The respective fractions were concentrated to obtain a solid residue, which was then converted into its hydrochloride with ethanolic hydrochloric acid and recrystallized from methanol/ethyl acetate to obtain the intended compound.

Example 20

1-Ethyl-4-(N-ethyl-4-methylsulfonylaminobenzoyl)-piperidine hydrochloride: 0.23 g Melting point: 188° to 191° C.

NMR (90 MHz, DMSO-$d_6$) 1.04 (3H, t, J=7H2) 1.28 (3H, t, J=7H2) 1.65-2.30 (4H, m) 2.60-3.95 (7H, m) 3.05 (3H, s) 3.78 (2H, q, J=7H2) 7.57 (2H, d, J=8H2) 8.06 (2H, d, J=8H2).

| Elementary analysis for $C_{17}H_{26}N_2O_3S \cdot HCl$: | | | |
|---|---|---|---|
| | C | H | N |
| calculated (%) | 54.45 | 7.27 | 7.47 |
| found (%) | 54.20 | 7.09 | 7.24 |

Example 21

1-Ethyl-4-(4-methylsulfonylaminobenzoyl)piperdine hydrochloride: 1.70 g

Melting point: 204° to 207° C.

NMR (90 MHz, DMSO-$d_6$) 1.27 (3H, t, J=7H2) 1.64-2.23 (4H, m) 2.62-3.90 (7H, m) 3.13 (3H, s) 7.34 (2H, d, J=8H2) 8.01 (2H, d, J=8H2) 10.42 (1H, brs).

| Elementary analysis for $C_{15}H_{22}N_2O_3S \cdot HCl$: | | | |
|---|---|---|---|
| | C | H | N |
| calculated (%) | 51.93 | 6.70 | 8.08 |
| found (%) | 51.76 | 6.57 | 7.86 |

Example 22

N-Methyl-4-(4-methylsulfonylaminobenzoyl)-1-[2-(3-pyridyl)ethyl]piperidine dihydrochloride 1.5 g (3.26 mmol) of 4-(4-methylsulfonylaminobenzoyl)-1-[2-(3-pyridyl)ethyl]piperidine dihydrochloride was added to a suspension of 0.242 g (10.08 mmol) of sodium hydride in 30 ml of dimethylformamide and the mixture was stirred at 60° C. for 5 h. 0.56 g (3.94 mmol) of methyl iodide was added thereto at room temperature and the obtained mixture was stirred at that temperature for 2 h. The liquid reaction mixture was filtered and the filtrate was concentrated to obtain a residue, which was purified according to silica gel chromatography (chloroform:methanol=97:3). This product was converted into its hydrochloride with ethanolic hydrogen chloride to obtain 0.5 g of the intended compound.

Melting point (°C.): ~182.

NMR (90 MHz, DMSO-$d_6$) δ: 1.8~2.4 (4H, m), 3.02 (3H, s), 3.31 (3H, s), 7.48 (2H, d, J=8 Hz), 7.98 (3H, m), 8.45 (1H, brd, J=7 Hz), 8.80 (2H, m).

Elementary analysis for $C_{21}H_{27}N_3O_3S \cdot 2HCl$: calculated: C, 53.16: H, 6.16: N, 8.86. found: C, 53.37: H, 6.12: N, 8.65.

Example 23

N-Butyl-4-(4-methylsulfonylbenzoyl)-1-[2-(3pyridyl)ethyl]piperidine dihydrochloride The same procedure as in Example 22 was repeated except that methyl iodide was replaced with n-butyl iodide and the obtained product was purified according to silica gel chromatography to obtain the intended compound having the following physical properties:

Melting point (°C.): 110 to 111.

NMR (90 MHz, CDCl$_3$) δ: 0.88 (3H, t), 1.2~3.3 (19H, m), 2.88 (3H, s), 3.73 (2H, t, J=8 Hz), 7.2 (1H, q, J=6, 6 Hz), 7.46 (2H, d, J=8 Hz), 7.5~7.64 (1H, m), 7.98 (2H, d, J=8 Hz), 8.46 (1H, dd, J=2, 6 Hz), 8.5 (1H, d, J=2 Hz).

| Elementary analysis for $C_{24}H_{33}N_3O_3S$: | | | |
|---|---|---|---|
| | C | H | N |
| calculated (%) | 64.97 | 7.51 | 9.47 |
| found (%) | 64.90 | 7.41 | 9.43 |

Example 24

4-(4-methylsulfonylaminophenyl)hydroxymethyl-1-(2-(2-pyridyl)ethyl)piperidine dihydrochloride 2.0 g (5.16 mmol) of 4-(4-methylsulfonylaminobenzoyl)-1-[2-(2-pyridyl)ethyl]piperidine was dissolved in 150 ml of methanol. 0.39 g of sodium borohydride was added to the solution under cooling with ice and the mixture was stirred at 0° C. for 1 h. The liquid reaction mixture was acidified by adding ethanolic hydrogen chloride dropwise thereto at 0° C. and an inorganic matter thus formed was filtered out. The filtrate was concentrated and the resulting residual oil was dissolved in ethanol. The solution was made alkaline with aqueous ammonia and an inorganic matter thus formed was further filtered out. The filtrate was concentrated and the obtained residual oil was purified according to silica gel chromatography (chloroform:methanol:aqueous ammonia=90:9:1). The oil thus obtained was converted into its hydrochloride in an ordinary manner to obtain 0.76 g of the intended compound.

Melting point (°C.): ~182.

NMR (90 MHz, DMSO-$d_6$) δ: 1.3~2.4 (4H, m), 2.92 (3H, s), 4.22 (1H, br), 7.23 (4H, m), 7.6~7.9 (2H, m), 8.28 (1H, dt, J=1, 7 Hz), 8.65 (1H, d, J=5 Hz), 9.64 (1H, s, D$_2$O exchange), 10.8 (1H, br, D$_2$O exchange).

| Elementary analysis for $C_{21}H_{29}N_3O_3S \cdot 2HCl$: | | | |
|---|---|---|---|
| | C | H | N |
| calculated (%) | 52.94 | 6.56 | 8.82 |
| found (%) | 53.16 | 6.83 | 8.61 |

Example 25

N-Methyl-4-(4-methylsulfonylaminobenzoyl)-1-[2-(3-pyridyl)ethyl]piperidine dihydrochloride (Another Process for Synthesizing the Compound of Example 22)

0.8 g (2.7 mmol) of N-methyl-4-(4-methylsulfonylaminobenzoyl)piperidine dihydrochloride, 0.52 g (2.7 mmol) of 3-(2-chloroethyl)pyridine hydrochloride, 3.0 g of potassium carbonate and 0.2 g of potassium iodide were dissolved in 15 ml of dimethylformamide and the solution was stirred at 90° C. for 3.5 h. After cooling, an inorganic matter was filtered out and the filtrate was concentrated to obtain a residue, which was purified according to silica gel chromatography (chloroform:methanol=97:3). The purified product was converted into its hydrochloride in an ordinary manner to obtain 0.6 g of the intended compound. The melting point and NMR signals of this product coincided with those of the compound obtained in Example 22.

Examples 26 to 115

Each compound listed in Tables 3 to 12 was obtained from the piperidine compound, the pyrrolidine compound and a halide compound thereof shown in Referential Examples 3 to 5 in the same way as shown in Examples 1 to 25.

A variety of compounds of the invention was obtained, including a heterocyclic ring or a condensed aromatic ring.

TABLE 3

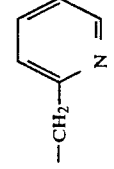

| Example | Y | m.p. (°C.) | Molecular formula | Elementary analysis calculated: (upper column) found: (lower column) | | | NMR |
|---|---|---|---|---|---|---|---|
| | | | | C | H | N | |
| 26 | —CH$_2$— 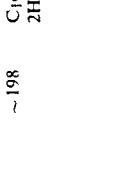 (2-pyridyl) | ~198 | C$_{19}$H$_{23}$N$_3$O$_3$S. 2HCl.H$_2$O | 49.14 48.96 | 5.86 5.84 | 9.05 8.89 | (400MHz, DMSO-d$_6$)δ: 1.9–2.1(4H, m)3.11(3H, s) 3.21(2H, m)3.46(2H, m)3.66(1H, m)4.48(2H, s) 7.31(2H, d, J=8.8)7.52(1H, dd, J=7.8, 4.9)7.68(1H, d, J=7.8)7.95(1H, dd, J=7.5, 1.5)7.98(2H, d, J=8.8) 8.70(1H, d, J=4.4)10.41(1H, s) |
| 27 | —CH$_2$— 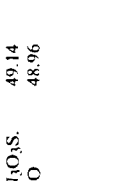 (3-pyridyl) | ~230 | C$_{19}$H$_{23}$N$_3$O$_3$S. 2HCl.½H$_2$O | 49.78 49.81 | 5.79 5.85 | 9.17 9.02 | (400MHz, DMSO-d$_6$)δ: 1.85–2.25(4H, m)3.11(3H, s) 4.48(2H, s)7.31(2H, d, J=8.8)7.88(1H, dd, J=5.7, 7.6) 7.99(2H, d, J=8.8)8.55(1H, d, J=7.3)9.05(1H, s) 10.41(1H, s)11.41(1H, br) |
| 28 | —(CH$_2$)$_2$— 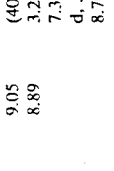 (2-pyridyl) | ~180 | C$_{20}$H$_{25}$N$_3$O$_3$S. 2HCl.½H$_2$O | 50.85 50.88 | 6.04 6.02 | 8.89 8.81 | (400MHz, DMSO-d$_6$)δ: 1.9–2.1(4H, m)3.12(3H, s) 3.18(2H, m)7.32(2H, d, J=8.8)7.66(1H, t, J=6.2) 7.75(1H, d, J=7.8)7.99(2H, d, J=8.8)8.21(1H, t, J=7.3) 8.71(1H, d, J=4.9)10.42(1H, s, D$_2$O exchange)10.84 1H, br, D$_2$O exchange) |
| 29 | —(CH$_2$)$_2$— 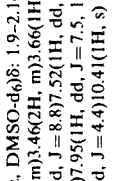 (4-pyridyl) | ~260 | C$_{20}$H$_{25}$N$_3$O$_3$S. 2HCl | 52.17 52.25 | 5.91 5.91 | 9.13 9.05 | (100MHz, DMSO-d$_6$)δ: 1.8–2.3(4H, m)3.13(3H, s) 7.32(2H, d, J=8)7.99(4H, m)8.88(2H, d, J=6) 10.46(1H, s, D$_2$O exchange)11.2(1H, br, D$_2$O exchange) |
| 30 | —(CH$_2$)$_3$— 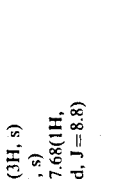 (2-pyridyl) | ~200 | C$_{21}$H$_{27}$N$_3$O$_3$S. 2HCl | 53.16 52.95 | 6.16 6.02 | 8.86 8.84 | (90MHz, DMSO-d$_6$)δ: 1.7–2.4(6H, m)3.10(3H, s) 7.24(2H, d, J=8)7.90(2H, d, J=8)7.95(1H, m) 8.42(1H, d, J=6)8.71(1H, d, J=4)8.81(1H, br) 10.36(1H, s, D$_2$O exchange)10.9(1H, br D$_2$O exchange) |
| 31 | —(CH$_2$)$_3$— 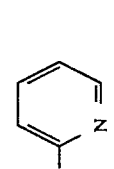 (3-pyridyl) | ~230 | C$_{21}$H$_{27}$N$_3$O$_3$S. 2HCl | 53.16 52.95 | 6.16 6.10 | 8.86 8.73 | (100MHz, DMSO-d$_6$)δ: 1.8–2.4(6H, m)3.10(3H, s) 7.30(2H, d, J=8)7.95(2H, d, J=8)7.97(2H, d, J=6) 8.83(2H, d, J=6)10.44(1H, br, D$_2$O exchange) 10.9–11.4(1H, br, D$_2$O exchange) |
| 32 | —(CH$_2$)$_4$— (3-pyridyl) | ~190 | C$_{22}$H$_{29}$N$_3$O$_3$S. 2HCl.H$_2$O | 52.17 52.15 | 6.57 6.34 | 8.30 8.27 | (90MHz, DMSO-d$_6$)δ: 1.5–2.2(8H, m)3.10(3H, s) 7.27(2H, d, J=8)7.82–8.06(3H, m)8.50(1H, d, J=7) 8.74(1H, d, J=5)8.84(1H, br) |

TABLE 3-continued

Structure: CH₃-S(=O)(=O)-NH-C₆H₄-C(=O)-[piperidine]-N-Y

| Example | Y | m.p. (°C.) | Molecular formula | Elementary analysis calculated: (upper column) found: (lower column) | | | NMR |
|---|---|---|---|---|---|---|---|
| | | | | C | H | N | |
| 33 | -(CH₂)₃-(3-pyridyl) | 217~ | C₂₁H₃₁N₃O₃S·2HCl | 54.96 / 54.70 | 6.63 / 6.54 | 8.36 / 8.21 | (90MHz, DMSO-d₆)δ: 1.1-2.3(10H, m)3.12(3H, s)7.34(2H, d, J=7)7.85-8.10(1H, m)8.00(2H, d, J=7)8.46(1H, d, t, J=2.7)8.79(1H, dd, J=2.5)8.86(1H, d, J=2)10.48(1H, s, D₂O exchange)10.90(1H, bs, D₂O exchange) |
| 34 | -CH(OH)-CH₂-(3-pyridyl) | ~140 | C₂₀H₂₅N₃O₄S·2HCl·1.2H₂O | 48.23 / 48.07 | 5.95 / 5.41 | 8.43 / 8.10 | (90MHz, DMSO-d₆)δ: 1.6-2.3(4H, m)3.12(3H, s)7.32(2H, d, J=8)8.01(2H, d, J=8)7.97(1H, m)8.54(1H, brd, J=6)8.88(2H, m)10.44(1H, br, D₂O exchange) |
| 35 | -CH₂-C(=O)-(3-pyridyl) | | C₂₀H₂₃N₃O₄S | 59.83 / 60.15 | 5.77 / 5.90 | 10.47 / 10.18 | (90MHz, CDCl₃)δ: 1.6-2.2(4H, m)3.06(3H, s)3.80(2H, s)7.30(2H, d, J=8)7.41(1H, m)7.92(2H, d, J=8)8.32(1H, dt, J=2.7)8.66(1H, dd, J=5.2)9.24(1H, d, J=2) |
| 36 | -CH(CH₃)-(4-pyridyl) | ~175 | C₂₀H₂₅N₃O₃S·2HCl·½H₂O | 50.85 / 50.70 | 6.04 / 5.78 | 8.89 / 8.54 | (90MHz, DMSO-d₆)δ: 1.75(3H, d, J=7)1.7-2.4(4H, m)3.11(3H, s)4.76(1H, br)7.24(2H, d, J=8)7.89(2H, d, J=8)8.20(2H, d, J=5)8.90(2H, d, J=5)10.33(1H, s, D₂O exchange)11.9(1H, br, D₂O exchange) |
| 37 | -CH(C₆H₅)-(4-pyridyl) | ~195 | C₂₅H₂₇N₃O₃S·2HCl | 57.47 / 57.33 | 5.59 / 5.62 | 8.04 / 8.31 | (90MHz, DMSO-d₆)δ: 1.7-2.4(4H, m)3.10(3H, s)6.13(1H, br, D₂O sharpen)7.24(2H, d, J=8)7.30(3H, m)7.93(4H, d, J=8)8.57(2H, d, J=5)8.90(2H, d, J=5)10.40(1H, s, D₂O exchange) |
| 38 | -CH₂-(6,7-dihydro-5H-cyclopenta[b]pyridin-7-yl) | ~140 | C₂₂H₂₇N₃O₃S·2HCl | 54.32 / 54.29 | 5.50 / 5.61 | 8.64 / 8.49 | (90MHz, DMSO-d₆)δ: 1.7-2.4(4H, m)3.12(3H, s)7.32(2H, d, J=8)7.48(1H, dd, J=6,8)8.00(3H, d, J=8)8.52(1H, d, J=6)10.43(1H, s) |

TABLE 3-continued

Structure:
CH₃—S(=O)(=O)—N(H)—[phenyl]—C(=O)—[piperidine]—N—Y

| Example | Y | m.p. (°C.) | Molecular formula | Elementary analysis calculated: (upper column) found: (lower column) | | | NMR |
|---|---|---|---|---|---|---|---|
| | | | | C | H | N | |
| 39 | −CH₂−CH=CH₂ (3-pyridyl) | ~200 | C₂₁H₂₅N₃O₃S·2HCl | 53.39 / 53.41 | 5.76 / 5.65 | 8.89 / 8.70 | (90MHz, DMSO-d₆)δ: 1.7−2.4(4H, m)3.09(3H, s)6.92(2H, m)7.25(2H, d, J=8)7.92(3H, m)8.57(1H, m)8.82(1H, d, J=5)9.00(1H, s) |
| 40 | −(CH₂)₂−S−(4-pyridyl) | ~195 | C₂₀H₂₅N₃O₃S₂·2HCl | 47.06 / 47.20 | 5.73 / 5.51 | 8.23 / 8.05 | (90MHz, DMSO-d₆)δ: 1.7−2.4(4H, m)3.09(3H, s)7.26(2H, d, J=8)7.94(2H, d, J=8)8.02(2H, d, J=6)8.60(2H, d, J=6) |
| 41 | −CH₂−(6-methyl-pyridin-3-yl) | 178~180 | C₂₀H₂₅N₃O₄S | 61.99 / 61.69 | 6.50 / 6.34 | 10.84 / 10.57 | (90MHz, CDCl₃)δ: 1.52−2.32(5H, m)2.55(3H, s)2.80−3.25(4H, m)3.09(3H, s)3.51(2H, s)7.14(1H, d, J=8), 7.31(2H, d, J=8.4)7.60(1H, dd, J=8, 2.2)7.91(2H, d, J=8.4)8.39(1H, d, J=2.2) |
| 42 | −CH₂−(2-chloro-pyridin-5-yl) | 181~183 | C₁₉H₂₂ClN₃O₃S | 55.94 / 55.88 | 5.44 / 5.47 | 10.30 / 9.97 | (90MHz, CDCl₃)δ: 1.60−2.30(6H, m)2.74−3.38(3H, m)3.10(3H, s)3.52(2H, s)7.26(2H, d, J=8)7.30(1H, d, J=8)7.69(1H, dd, J=8, 2.2)7.94(2H, d, J=8.8)8.30(1H, d, J=2.2) |
| 43 | −CH₂− (phenyl) | ~150 | C₂₀H₂₄N₂O₃S·HCl·½H₂O | 57.07 / 56.83 | 6.30 / 6.20 | 6.65 / 6.45 | (100MHz, DMSO-d₆)δ: 1.8−2.2(4H, m)3.12(3H, s)4.29(2H, s)7.30(2H, d, J=8)7.28−7.70(5H, m, D₂O sharpen)7.99(2H, d, J=8)10.42(1H, br, D₂O exchange)10.80(1H, br, D₂O exchange) |
| 44 | −(CH₂)₂− (phenyl) | 222~224 | C₂₁H₂₆N₂O₃S·HCl | 59.63 / 59.61 | 6.43 / 6.36 | 6.62 / 6.55 | (100MHz, DMSO-d₆)δ: 1.8−2.3(4H, m)3.12(3H, s)7.28(5H, s)7.32(2H, d, J=8)7.96(2H, d, J=8)10.3−11.0(2H, br, D₂O exchange) |
| 45 | −(CH₂)₃− (phenyl) | 215~217 | C₂₂H₂₈N₂O₃S·C₂H₂O₄ | 58.76 / 58.97 | 6.16 / 6.16 | 5.71 / 5.82 | (100MHz, DMSO-d₆)δ: 1.6−2.2(4H, m)3.12(3H, s)7.24(5H, m)7.31(2H, d, J=8)7.97(2H, d, J=8)8.35(2H, br) |

TABLE 3-continued

![structure: CH₃-S(=O)(=O)-N(H)-C₆H₄-C(=O)-piperidine-N-Y]

| Example | Y | m.p. (°C.) | Molecular formula | Elementary analysis calculated: (upper column) found: (lower column) | | | NMR |
|---|---|---|---|---|---|---|---|
| | | | | C | H | N | |
| 46 | –CH₂–(2-Cl-C₆H₄) | ~193 | C₂₀H₂₅N₂O₃S·HCl | 54.18 / 54.31 | 5.40 / 5.48 | 6.32 / 5.92 | (100MHz, DMSO-d₆)δ: 1.8–2.2(4H, m)3.12(3H, s)4.45(2H, s, D₂O sharpen)7.30(2H, d, J=8)7.40–7.50(4H, m)7.99(3H, m)10.45(1H, brs, D₂O exchange)11.2(1H, br, D₂O exchange) |
| 47 | –(CH₂)₂–(4-Cl-C₆H₄) | ~220 | C₂₂H₂₅ClN₂O₃S·HCl | 55.14 / 55.43 | 5.73 / 5.68 | 6.12 / 5.74 | (100MHz, DMSO-d₆)δ: 1.8–2.2(4H, m)3.12(3H, s)7.20–7.50(6H, m, D₂O sharpen→7.39(4H, s)&7.52(2H, d, J=8)8.00(2H, d, J=8)10.0–11.0(1H, br, D₂O exchange) |
| 48 | –(CH₂)₂–(4-F-C₆H₄) | ~220 | C₂₁H₂₅FN₂O₃S·HCl·1H₂O | 56.43 / 56.43 | 5.86 / 5.99 | 6.27 / 6.42 | (100MHz, DMSO-d₆)δ: 1.8–2.2(4H, m)3.12(3H, s)7.00–7.45(5H, m)8.00(2H, d, J=8)10.0–11.5(2H, br, D₂O exchange) |
| 49 | –(CH₂)₂–(4-CH₃-C₆H₄) | ~230 | C₂₂H₂₈N₂O₃S·HCl | 60.47 / 60.78 | 6.69 / 6.72 | 6.41 / 5.84 | (100MHz, DMSO-d₆)δ: 1.8–2.2(4H, m)2.27(3H, s)3.12(3H, s)7.16(4H, s)7.34(2H, d, J=8.0)8.01(2H, d, J=8)10.50(1H, br, D₂O exchange)10.5–11.5(1H, br, D₂O exchange) |
| 50 | –(CH₂)₂–(4-OCH₃-C₆H₄) | ~225 | C₂₂H₂₈N₂O₄S·HCl | 58.33 / 58.48 | 6.45 / 6.40 | 6.18 / 5.68 | (100MHz, DMSO-d₆)δ: 1.8–2.2(4H, m)3.12(3H, s)3.74(3H, s)6.88(2H, d, J=8)7.20(2H, d, J=8)7.32(2H, d, J=8)8.01(2H, d, J=8)10.0–11.0(2H, br, D₂O exchange) |
| 51 | –(CH₂)₂–(3,4-di-OCH₃-C₆H₃) | 190~191 | C₂₃H₃₀N₂O₅S·HCl | 57.19 / 57.27 | 6.47 / 6.43 | 5.80 / 5.77 | (90MHz, DMSO-d₆)δ: 1.8–2.4(4H, m)3.12(3H, s)3.72(3H, s)3.75(3H, s)6.7–7.0(3H, m)7.32(2H, d, J=8)8.0(2H, d, J=8)10.6(1H, br) |

TABLE 3-continued

Structure: CH₃-S(O)(O)-NH-[phenyl]-C(=O)-[piperidine with N-Y]

| Example | Y | m.p. (°C.) | Molecular formula | Elementary analysis calculated: (upper column) found: (lower column) | | | NMR |
|---|---|---|---|---|---|---|---|
| | | | | C | H | N | |
| 52 | —(CH₂)₂—[phenyl]—OH | 219~221 | C₂₁H₂₀N₂O₁S·HCl | 57.46 / 57.60 | 6.20 / 6.19 | 6.38 / 6.46 | (100MHz, DMSO-d₆)δ: 1.8-2.2(4H, m)3.15(3H, s)6.63(2H, d, J=8)7.08(2H, d, J=8)7.33(2H, d, J=8)8.00(2H, d, J=8)9.43(1H, s, D₂O exchange) |
| 53 | —CH₂—CH(OH)—[phenyl] | 133~135 | C₂₁H₂₀N₂O₄S·CH₃SO₂H·½H₂O | 52.37 / 51.99 | 6.13 / 5.65 | 5.55 / 5.51 | (100MHz, DMSO-d₆)δ: 1.7-2.3(4H, m)3.12(3H, s)7.31(2H, d, J=8)7.42(5H, s)8.0(2H, d, J=8)10.38(1H, s) |
| 54 | —CH₂—CH(OH)—[phenyl]—NH—SO₂CH₃ | 223~226 | C₂₂H₂₉N₃O₆S₂·HCl | 49.66 / 49.73 | 5.68 / 5.60 | 7.90 / 7.81 | (90MHz, DMSO-d₆)δ: 1.7-2.3(4H, m)3.04(3H, s)3.08(3H, s)7.20(4H, d, J=8)7.52(2H, d, J=8)7.90(2H, d, J=8)9.98(1H, s, D₁O exchange)10.2(1H, br, D₂O exchange)10.3(1H, s, D₂O exchange) |
| 55 | —CH₂—C(=O)—[phenyl]—NH—SO₂CH₃ | ~220 | C₂₂H₂₇N₃O₆S₂·HCl·H₂O | 48.21 / 48.13 | 5.52 / 5.23 | 7.67 / 7.68 | (400MHz, DMSO-d₆)δ: 1.9-2.2(4H, m)3.12(3H, s)3.15(2H, s)5.03(2H, s)7.34(2H, d, J=8.3)7.38(2H, d, J=8.3)7.99(2H, d, J=8.8)8.02(2H, d, J=8.3)10.18(1H, brs, D₂O exchange)10.47(1H, s, D₂O exchange)10.64(1H, s, D₂O exchange) |
| 56 | —CH₂—[thiophene] | 173~175 | C₁₈H₂₂N₂O₃S₂·CH₃SO₃H | 48.08 / 48.24 | 5.52 / 5.46 | 5.90 / 5.86 | (100MHz, DMSO-d₆)δ: 1.7-2.2(4H, m)2.38(3H, s)3.12(3H, s)4.60(2H, s, D₂O sharpen)7.10-7.40(4H, m)7.74(1H, d, J=4)8.00(2H, d, J=8)9.7(1H, br, D₂O exhange)10.39(1H, br, D₂O exchange) |
| 57 | —(CH₂)₂—[thiophene] | 219~221 | C₁₉H₂₁N₂O₃S₂·CH₃SO₃H | 49.16 / 49.18 | 5.78 / 5.66 | 5.73 / 5.72 | (100MHz, DMSO-d₆)δ: 1.7-2.2(4H, m)2.37(3H, s)3.12(3H, s)7.01(2H, d, J=4)7.32(2H, d, J=8)7.40(1H, t, J=4)8.01(2H, d, J=8)10.2(1H, br, D₂O exchange) |

TABLE 3-continued

Structure header:

CH₃—S(=O)(=O)—NH—[phenyl]—C(=O)—[piperidine]—N—Y

| Example | Y | m.p. (°C.) | Molecular formula | Elementary analysis calculated: (upper column) found: (lower column) | | | NMR |
|---|---|---|---|---|---|---|---|
| | | | | C | H | N | |
| 58 | 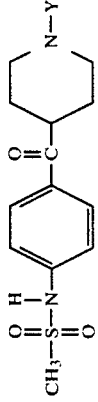 —CH₂— (naphthalene) | 220~222 | C₂₄H₂₆N₂O₃S·CH₃SO₃H | 57.90 58.09 | 5.83 5.72 | 5.40 4.94 | (100MHz, DMSO-d₆)δ: 1.7–2.1(4H, m)2.39(3H, s)3.12(3H, s)4.93(2H, s)7.32(2H, d, J=8)7.50–8.20(8H, m)8.32(1H, brd, J=7) |
| 59 | 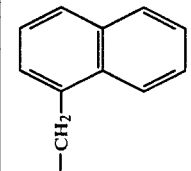 —(CH₂)₂— (5-ethylpyridin-2-yl) | 208~ | C₂₂H₂₉N₃O₃S·2HCl | 54.10 53.09 | 6.40 6.39 | 8.60 8.48 | (90MHz, DMSO-d₆)δ: 1.13(3H, t, J=8)2.77(2H, q, J=8)3.12(3H, s)7.34(2H, d, J=8)7.87(1H, d, J=7)8.02(2H, d, J=8)8.33(1H, dd, J=2.7)8.70(1H, d, J=2) |
| 60 | 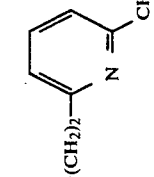 —(CH₂)₂— (6-methylpyridin-2-yl) | 172~174 | C₂₁H₂₇N₃O₃S | 62.80 62.88 | 6.79 6.76 | 10.47 10.37 | (90MHz, CDCl₃)δ: 2.53(3H, s)3.10(3H, s)6.15(1H, s, D₂O exchange)6.97(2H, dd, J=2.7)7.27(2H, d, J=8)7.48(1H, t, J=7)7.94(2H, d, J=8) |
| 61 | 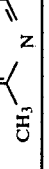 —(CH₂)₂—C(CH₃)=N (thiazole) | ~167 | C₁₉H₂₅N₄O₃S·2HCl | 47.49 47.69 | 5.67 5.78 | 8.7 8.27 | (90MHz, DMSO-d₆)δ: 1.7–2.3(4H, m)2.39(3H, s)3.10(3H, s)7.26(2H, d, J=8)7.93(2H, d, J=8)9.07(1H, s)10.37(1H, s, D₂O exchange)11.2(1H, br, D₂O exchange) |

TABLE 4

$$R^1-\underset{\underset{O}{\|}}{\overset{\overset{O}{\|}}{S}}-\underset{R^3}{N}-\underset{}{\text{phenyl}}-X-\text{piperidine}-N-Y$$

| Example | R¹ | R³ | X | Y | m.p. (°C.) | Molecular formula | C (calc/found) | H (calc/found) | N (calc/found) | NMR |
|---|---|---|---|---|---|---|---|---|---|---|
| 62 | C₂H₅— | H | —C(=O)— | —CH₂—(4-pyridyl) | ~217 | C₂₀H₂₅N₃O₃S·2HCl·½H₂O | 61.50 / 51.50 | 5.06 / 6.15 | 9.00 / 8.94 | (100MHz, DMSO-d₆)δ:1.18, (3H, t, J=7)1.7–2.3(4H, m) 3.18(2H, q, J=7)4.59(2H, s) 7.30(2H, d, J=8)7.94(2H, d, J=8)8.30(2H, d, J=6)8.96(2H, d, J=G)10.41(1H, s, D₂O exchange)11.5–12.5(1H, br, D₂O exchange) |
| 63 | C₂H₃— | H | —C(=O)— | —(CH₂)₂—phenyl | | C₂₂H₂₈N₂O₃S·HCl·H₂O | 58.07 / 57.57 | 6.87 / 6.55 | 6.16 / 6.49 | (100MHz, DMSO-d₆)δ:1.20 (3H, t, J=7)1.6—2.2(4H, m) 3.20(2H, q, J=7)7.2–7.6(6H, m) 7.96(2H, d, J=8)10.4(1H, br, D₂O exchange) |

TABLE 5

$$CH_3-\underset{\underset{O}{\|}}{\overset{\overset{O}{\|}}{S}}-\underset{H}{N}-\text{phenyl}(R^2)-\underset{\underset{}{\|}}{\overset{\overset{O}{\|}}{C}}-\text{piperidine}-N-Y$$

| Example | R² | Y | m.p. (°C.) | Molecular formula | C (calc/found) | H (calc/found) | N (calc/found) | NMR |
|---|---|---|---|---|---|---|---|---|
| 64 | —OH | —CH₂—(4-pyridyl) | ~208 | C₁₉H₂₃N₃O₃S·2HCl | 49.35 / 49.30 | 5.45 / 5.39 | 9.09 / 8.95 | (100MHz, DMSO-d₆)δ:1.8–2.2(4H, m)3.15 3H, s)4.64(2H, s)6.78(2H, m)7.95(1H, d, J=8)8.27(2H, d, J=6)8.97(2H, d, J=6) 10.55(1H, s, D₂O exchange)12.1(2H, br, D₂O exchange) |
| 65 | —OH | —(CH₂)₂—phenyl | ~240 | C₂₁H₂₆N₂O₄S·HCl·½H₂O | 56.68 / 56.82 | 6.27 / 6.07 | 6.29 / 6.25 | (100MHz, DMSO-d₆)δ:1.8–2.2(4H, m) 3.16(3H, s)6.77(1H, d, J=8)6.82(1H, s) 7.32(5H, s)7.94(1H, d, J=8)10.54(1H, s, D₂O exchange)11.0(1H, br, D₂O exchange) 12.13(1H, s, D₂O exchange) |
| 66 | —OCH₃ | —CH₂—(4-pyridyl) | ~205 | C₂₀H₂₁N₃O₂S·2HCl·⅜H₂O | 49.19 / 49.01 | 5.80 / 5.58 | 8.60 / 8.11 | (100MHz, DMSO-d₆)δ:1.7–2.3(4H, m) 3.13(3H, s)3.88(3H, s)4.61(2H, s)6.08(1H, dd, J=7, 1)7.97(1H, d, J=1)8.58(1H, d, J=7) 9.35(2H, d, J=6)10.00(2H, d, J=6) |

TABLE 6

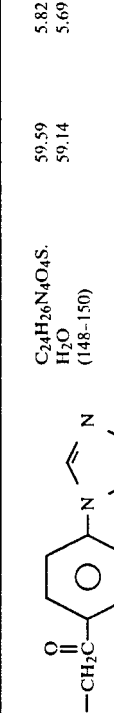

| Example | Y | Molecular formula (m.p. °C.) | Elementary analysis calculated: (upper column) found: (lower column) | | | ¹HNMR δ (90 MHz unless otherwise stated) |
|---|---|---|---|---|---|---|
| | | | C | H | N | |
| 67 | 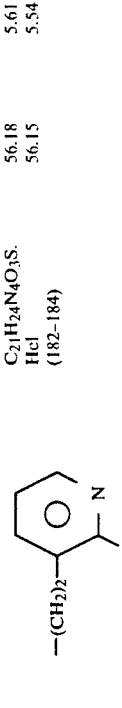 | C₂₄H₂₆N₄O₄S. H₂O (148–150) | 59.59<br>59.14 | 5.82<br>5.69 | 11.56<br>11.27 | (DMSO-d₆)2.2–3.7(5H, m)3.10(3H, s) 3.85(2H, s)7.15(1H, brs)7.28(2H, d, J=8)7.75–8.05(5H, m)8.16(2H, d, J=8)8.43(1H, brs) |
| 68 | 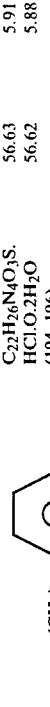 | C₂₁H₂₄N₄O₃S. Hcl (182–184) | 56.18<br>56.15 | 5.61<br>5.54 | 12.48<br>12.31 | (DMSO-d₆)1.8–2.4(4H, m)2.6–4.0(9H, m)3.12(3H, s)7.32(2H, d, J=8) 7.76(1H, dd, J=8, 5)8.00(2H, d, J=8)8.10(1H, brd, J=8)8.68(1H, brd, J=5)10.41(1H, brs)10.7(1H, br) |
| 69 | 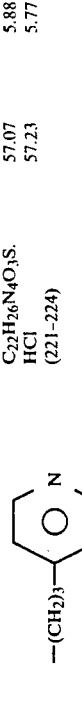 | C₂₂H₂₆N₄O₃S. HCl.0.2H₂O (194–196) | 56.63<br>56.62 | 5.91<br>5.88 | 12.01<br>11.68 | (DMSO-d₆)1.8–2.4(4H, m)2.6–4.0(11H, m)3.12(3H, s)7.34(2H, d, J=8) 7.72(1H, dd, J=8.5)7.98(2H, d, J=8)8.08(1H, dd, J=8, 2)8.65 (1H, dd, J=5, 2)10.49(1H, brs) 10.8(1H, br) |
| 70 | 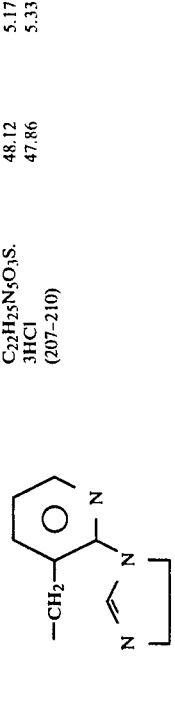 | C₂₂H₂₆N₄O₃S. HCl (221–224) | 57.07<br>57.23 | 5.88<br>5.77 | 12.10<br>11.76 | (DMSO-d₆)1.8–2.4(4H, m)2.6–3.9(11H, m)7.67(1H, dd, J=5, 2)7.99(2H, d, J=8)8.02(1H, brs)8.68(1H, d, J=5)10.47(1H, br)10.80(1H, br) |
| 71 | | C₂₂H₂₅N₅O₃S. 3HCl (207–210) | 48.12<br>47.86 | 5.17<br>5.33 | 12.76<br>12.71 | (CDCl₃; free form)1.62–2.38(6H, m) 2.78–3.60(3H, m)3.02(3H, s)3.42 (2H, s)7.17(1H, s), 7.30(3H, m) 7.32(2H, d, J=9.0)7.64(1H, s), 7.88(1H, dd, J=2.0, 4.5), 7.90(1H, d, J=2.0)8.22(1H, s)8.46(1H, dd, J=2.0, 4.2) |

TABLE 6-continued

| | | CH₃-S(=O)(=O)-NH-[phenyl]-C(=O)-[cyclohexyl]-N-Y | | | |
|---|---|---|---|---|---|
| 72 | -CH₂-[N-methylpyridyl] | C₁₉H₂₅N₃O₃S<br>(144-145) | 60.78<br>60.65 | 6.71<br>6.62 | 11.19<br>11.17 | (DMSO-d₆)1.4-2.3(6H, m)2.86(2H, m)3.0-3.3(1H, m)3.09(3H, s)3.39(2H, s)3.57(3H, s)5.85(2H, d-like, J=2)6.63(1H, t, J=2)7.28(2H, d, J=8)7.94(2H, d, J=8) |
| 73 | -(CH₂)₃-[imidazolyl] | C₁₉H₂₆N₄O₃S·2HCl<br>(187-190) | 49.23<br>49.37 | 6.10<br>6.31 | 12.09<br>12.13 | (CDCl₃; free from)1.70-2.40(10H, m)2.75-3.32(3H, m)3.04(3H, s)4.00(2H, t, J=7.2)6.02(1H, s)6.08(1H, s)7.00(1H, s)7.28(2H, d, J=8.7)7.53(1H, s)7.83(2H, d, J=8.7) |
| 74 | -(CH₂)₂-[pyridazinyl] | C₁₉H₂₄N₄O₃S·0.2H₂O<br>(156-157) | 58.20<br>58.24 | 6.17<br>6.16 | 14.29<br>14.20 | (DMSO-d₆)1.4-2.04(4H, m)2.16(2H, m)2.6-3.6(7H, m)3.10(3H, s)7.28(2H, d, J=8)7.59(2H, d, J=8)9.06(1H, t, J=3)(2H, d, J=3)7.94 |
| 75 | -CH₂C(=CH₂)-[pyridyl] | C₂₀H₂₄N₄O₃S<br>(157-158) | 59.98<br>59.94 | 6.04<br>6.01 | 13.99<br>13.78 | (DMSO-d₆)1.4-2.04(4H, m)2.0-2.4(2H, m)2.94(2H, m)3.10(3H, s)3.32(1H, m)3.45(2H, s)5.63(1H, brs)6.33(1H, d, J=2)7.28(2H, d, J=8)7.74(1H, dd, J=1, 5)7.94(2H, d, J=8)8.77(1H, d, J=5)9.12(1H, d, J=1) |
| 76 | -CH₂-[pyrazinyl] | C₁₈H₂₂N₄O₃S·2HCl<br>(210-212) | 48.31<br>48.46 | 5.42<br>5.29 | 12.53<br>12.49 | (DMSO-d₆)1.75-2.35(4H, m)3.12(3H, s)2.80-3.85(5H, m)4.52(2H, s)7.33(2H, d, J=8)7.99(2H, d, J=8)8.77(2H, s)9.00(1H, s)10.43(1H, s) |
| 77 | -(CH₂)₂-[pyrazinyl] | C₁₉H₂₄N₄O₃S·½(COOH)₂<br>(195-196) | 55.40<br>55.13 | 5.82<br>5.82 | 12.93<br>12.75 | (DMSO-d₆)1.5-2.1(4H, m)2.2-3.8(9H, m)3.11(3H, s)7.30(2H, d, J=8)7.96(2H, d, J=8)8.43-8.63(3H, m) |

TABLE 6-continued

| | | | | | |
|---|---|---|---|---|---|
| 78 | ![structure with CN, C=O, H3C, pyridinone]<br>-CH2 | C22H24N4O5S.<br>HCl.1.2H2O<br>(210-decomp.) | 51.35<br>51.30 | 5.37<br>5.7 | 10.89<br>10.70 | (DMSO-d6)1.8–2.2(4H, m)2.66(3H, s)<br>3.10(3H, s)4.84(2H, s)7.32(2H, d,<br>J=8)8.00(2H, d, J=8)8.68(1H, s)<br>10.41(1H, s)12.5–13.5(1H, br) |
| 79 | ![structure with NH, C=O]<br>-CH2 | C18H22N4O5S<br>(232–234) | 53.19<br>53.25 | 5.46<br>5.44 | 13.78<br>13.75 | (DMSO-d6)1.4–2.0(4H, m)2.30(2H, m)<br>2.88(2H, m)3.10(3H, s)3.20(2H, s)<br>5.45(1H, s)7.28(2H, d, J=8)<br>7.95(2H, d, J=8) |
| 80 | ![structure with NH]<br>-(CH2)2 | C23H26N4O3S.<br>HCl.1.5H2O<br>(165–167) | 56.61<br>56.63 | 6.19<br>5.85 | 8.61<br>8.42 | (100MHz, DMSO-d6)1.8–2.2(4H, m)3.12<br>(3H, s)6.9–7.15(2H, m)7.15–7.45<br>(4H, m)7.63(1H, dd-like, J=6, 2)<br>7.99(2H, d, J=8)10.5(1H, br)<br>10.97(1H, brs)etc. |
| 81 | ![phthalimide structure]<br>-(CH2)2-N | C23H25N3O5S<br>(204–205) | 60.64<br>60.71 | 5.53<br>5.56 | 9.22<br>9.24 | (DMSO-d6)1.64(4H, m)2.14(2H, m)<br>2.5–3.6(5H, m)3.10(3H, s)3.71(2H,<br>t, J=7)7.28(2H, d, J=8)7.85<br>(4H, s)7.93(2H, d, J=8) |
| 82 | ![indole structure]<br>-CH2 | C23H25N3O3S.<br>2HCl<br>(−205 decomp.) | 55.65<br>55.76 | 5.48<br>5.57 | 8.46<br>8.59 | (400MHz, DMSO-d6)2.02(4H, m)3.11<br>(3H, s)3.30(2H, m)3.50–3.70(3H, m)<br>4.68(2H, s)7.31(2H, d, J=8.8)<br>7.70(1H, t, J=6.8)7.82–7.88(2H, m)<br>7.98(2H, d, J=8.8)8.07(1H, d, J=<br>8.3)8.10(1H, d, J=8.8)8.53(1H, d,<br>J=8.3)10.42(1H, s)10.83(1H, br) |
| 83 | ![tetrahydroquinoline structure]<br>-CH2 | C23H25N3O3S.<br>2HCl.0.7H2O<br>(−205 decomp.) | 54.27<br>54.10 | 5.62<br>5.54 | 8.25<br>8.09 | (100MHz, DMSO-d6)1.7–2.4(4H, m)<br>3.12(3H, s)7.30(2H, d, J=8)<br>7.68–8.44(6H, m)9.19(1H, brs)<br>9.48(1H, d, J=1)10.47(1H, s)<br>11.6(1H, br) |

TABLE 6-continued

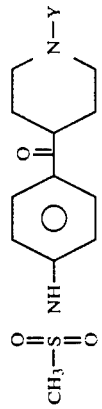

| Example | Y | Melting point | Structural formula | Elementary analysis (C.H.N.) calculated: (upper column) found: (lower column) | ¹HNMR (90 MHz unless otherwise stated) |
|---|---|---|---|---|---|
| 84 | 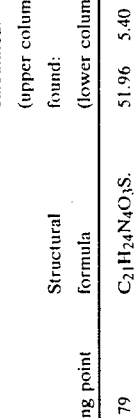 | 176–179 | C₂₁H₂₄N₄O₃S·2HCl | 51.96  5.40  11.54<br>51.96  5.40  11.54 | (DMSO-d₆)1.8–2.4(4H, m)3.12(3H, s) 4.63(2H, s)7.32(2H, d, J=8)7.45 (1H, m)7.95(4H, m)8.57(1H, s) 9.00(1H, d, J=7)etc. |
| 85 |  | 220–222 | C₂₁H₂₄N₄O₃S·2HCl | 51.96  5.40  11.54<br>51.74  5.41  11.29 | (400MHz, DMSO-d₆)1.75–2.20(4H, m) 3.11(3H, s)3.20–3.90(5H, m) 4.50(2H, s)7.31(2H, d, J=8.5) 7.97(2H, d, J=8.5)8.07(1H, d, J= 9.3)8.20–8.32(2H, m)8.46(1H, s) 9.14(1H, s)10.42(1H, s)11.6(1 H, br) |
| 86 |  | 255–257 | C₂₁H₂₄N₄O₃S | 61.15  5.86  13.58<br>61.10  6.00  13.29 | (DMSO-d₆)1.69(4H, m)2.0–3.6(5H, m) 3.09(3H, s)3.75(2H, s)7.12(2H, dd, J=6, 3)7.28(2H, d, J=8)7.50 (2H, dd, J=6, 3)7.95(2H, d, J=8) |
| 87 | 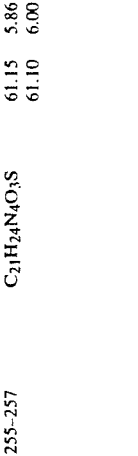 | 171–173 | C₂₂H₂₈N₆O₅S | 54.09  5.78  17.20<br>54.17  5.80 | (DMSO-d₆)1.4–2.0(4H, m)2.0–3.6(7H, m)3.10(3H, s)3.22(3H, s)3.42(3H, s)4.36(2H, t, J=7)7.28(2H, d, J= 8)7.94(2H, d, J=8)8.03(1H, s) |

TABLE 6-continued

| | | | | | | | | |
|---|---|---|---|---|---|---|---|---|
| 88 | [tricyclic structure with -CH₂- linker] | 238-240 | C₂₆H₂₆N₂O₃S | 69.93 69.59 | 5.87 5.93 | 6.27 6.27 | | (CDCl₃)1.60-1.92(4H, m)2.50-3.18 (5H, m)3.07(1H, s)4.87(1H, s) 7.19(2H, d, J=8.8)7.20-7.40(4H, m) 7.59-7.76(4H, m) |
| 89 | —(CH₂)₃CH₃ | 259-262 | C₁₇H₂₆N₂O₃S·HCl | 54.45 54.54 | 7.27 7.12 | 7.47 7.40 | | (DMSO-d₆)0.93(3H, t, J=7) 1.07-2.35(8H, m)2.60-3.95(7H, m) 3.12(3H, s)7.32(2H, d, J=8) 7.99(2H, d, J=8)10.22(1H, brs) |
| 90 | [cyclohexyl-CH₂-] | −260 (decomp.) | C₂₀H₃₀N₂O₃S·HCl | 57.87 57.62 | 7.54 7.41 | 6.75 6.54 | | (DMSO-d₆)0162-2.43(15H, m)2.60-3.95 (7H, m)3.12(3H, s)7.33(2H, d, J=8) 8.00(2H, d, J=8)10.43(1H, brs) |
| 91 | —CH₂C(=CH₂)—CH₃ | 221-224 | C₁₇H₂₄N₂O₃S·HCl | 54.74 54.81 | 6.77 6.75 | 7.51 7.50 | | (DMSO-d₆)1.80-2.38(4H, m)1.88(3H, s) 2.60-3.80(5H, m)3.09(3H, s) 3.61(2H, s)4.19(2H, s)4.19(2H, s)7.24(2H, d, J=8)7.90(2H, d, J=8)10.32(1H, brs) |
| 92 | —CH₂COOEt | 159-162 | C₁₇H₂₄N₂O₅S·(COOH)₂ | 49.76 50.11 | 5.73 5.17 | 6.11 6.14 | | (DMSO-d₆)1.21(3H, t, J=7)1.38-2.02 (4H, m)2.50-3.78(5H, m)3.08(3H, s) 3.61(2H, s)4.11(2H, q, J=7) 6.95(2H, brs)7.22(2H, d, J=8) 7.88(2H, d, J=8) |
| 93 | —CN | 205-207 | C₁₄H₁₇N₃O₃S | 54.71 54.61 | 5.57 5.51 | 13.67 13.51 | | (DMSO-d₆)1.5-2.04(4H, m)2.95-3.70 (5H, m)3.08(3H, s)7.21(2H, d, J=8) 7.88(2H, d, J=8)10.22(1H, brs) |
| 94 | —CH₂CN | 178-180 | C₁₅H₁₉N₃O₃S | 56.06 55.78 | 5.96 5.83 | 13.07 12.83 | | (DMSO-d₆)1.4-2.0(4H, m)2.2-3.6(5H, m)3.12(3H, s)3.74(2H, s)7.33(2H, d, J=8)8.02(2H, d, J=8) |
| 95 | —(CH₂)₃CN | 201-203 | C₁₇H₂₃N₃O₃S·HCl | 52.91 52.80 | 6.27 6.13 | 10.89 10.68 | | (DMSO-d₆)1.7-2.4(4H, m)2.4-4.0 (11H, m)3.12(3H, s)7.36(2H, d, J=8)8.02(2H, d, J=8)10.48(1H, br) 10.9(1H, br) |

TABLE 6-continued

| | | CH₃-S(=O)(=O)-NH-[phenyl]-C(=O)-[cyclohexyl]-N-Y | | | | | NMR |
|---|---|---|---|---|---|---|---|
| 96 | -(CH₂)₂-N(Et)(Et) | 194-196 | $C_{19}H_{31}N_3O_3S \cdot 2(COOH)_2$ | 48.68<br>48.60 | 6.33<br>6.40 | 7.40<br>7.32 | (DMSO-$d_6$)1.16(6H, t, J=7)1.4-2.0(4H, m)3.08(3H, s)7.22(2H, d, J=8)7.92(2H, d, J=8)etc. |
| 97 | -(CH₂)₂-N[piperidine] | 198-202 | $C_{20}H_{31}N_3O_3S \cdot 2(COOH)_2$ | 50.25<br>50.15 | 6.15<br>6.13 | 7.33<br>7.21 | (DMSO-$d_6$)1.3-2.0(10H, m)2.4-3.6(13H, m)3.08(3H, s)7.21(2H, d, J=8)7.84(2H, d, J=8) |
| 98 | -(CH₂)₂-N[morpholine] | 217-219 | $C_{19}H_{29}N_3O_4S \cdot 2(COOH)_2 \cdot 1.3H_2O$ | 46.12<br>46.18 | 5.99<br>6.10 | 7.01<br>6.77 | (DMSO-$d_6$)1.6-2.1(4H, m)3.12(3H, s)7.30(2H, d, J=8)7.07(2H, d, J=8) etc. |
| 99 | -(CH₂)₃-N[piperidine] | 223-225 | $C_{21}H_{33}N_3O_3S \cdot 2(COOH)_2$ | 51.10<br>51.38 | 6.35<br>6.53 | 7.15<br>7.54 | (DMSO-$d_6$)1.3-2.4(12H, m)3.12(3H, s)7.29(2H, d, J=8)7.96(2H, d, J=8) etc. |

TABLE 7

Structure: CH3-C6H4-SO2-NH-C6H4-C(=O)-[piperidine]-N-Y

| Example | Y | Melting point | Structural formula Elementary analysis (C.H.N.) calculated: (upper column) found: (lower column) | ¹H NMR |
|---|---|---|---|---|
| 100 | −(CH₃)₃-[pyridine-N] | 162–165 | C₂₇H₃₁N₃O₃S·2HCl·3H₂O<br>53.64  6.50  6.95<br>53.73  6.14  6.74 | (DMSO-d₆)1.7–2.4(6H, m)2.33(3H, s)<br>2.7–3.9(9H, m)7.25(2H, d, J=8)<br>7.36(2H, d, J=8)7.76(2H, d,<br>J=8)7.89(2H, d, J=8)7.99(2H,<br>d, J=6)8.86(2H, d, J=6)11.01<br>(1H, brs)11.20(1H, br) |
| 101 | −(CH₂)₂-[pyridine with CH₃] | 192–195 | C₂₇H₃₁N₃O₃S·2HCl·0.2H₂O<br>58.52  6.07  7.58<br>58.55  6.02  7.40 | (DMSO-d₆)1.8–2.1(4H, m)2.33(3H, s)<br>2.73(3H, s)2.2–3.9(9H, m)7.24<br>2H, d, J=8)7.35(2H, d, J=8)<br>7.64–7.81(2H, m)7.75(2H, d, J=8)<br>7.89(2H, d, J=8)8.31(1H, t, J=<br>7)10.77(1H, brs)11.20(1H, br) |

TABLE 8

Structure: CH₃SO₂NH-C₆H₄-CH₂-[piperidine]-N-Y

| Example | Y | Melting point | Structural formula Elementary analysis | ¹H NMR |
|---|---|---|---|---|
| 102 | −(CH₂)₂-[pyridine] | 156–157 | C₂₀H₂₇N₃O₂S<br>64.31  7.29  11.25<br>64.48  7.22  11.21 | (DMSO-d₆)0.9–2.0(5H, m)2.90(3H, s)<br>7.18(1H, dd, J=7.5)7.02(4H, s)<br>7.53(1H, brd, J=7)8.28(2H, m)<br>etc. |
| 103 | −(CH₂)₂-[phenyl-OCH₃, OCH₃] | 202–204 | C₂₃H₃₂N₂O₄S·(COOH)₂<br>57.50  6.56  5.36<br>57.17  6.50  5.35 | (DMSO-d₆)1.2–2.0(5H, m)2.91(3H, s)<br>3.67(3H, s)3.69(3H, s)6.56–6.90<br>3H, m)7.06(4H, s)etc. |

TABLE 9

Structure: CH₃SO₂NH-C₆H₄-C(=O)-[cyclic]-N-Y

| Example | Y | Melting point | Structural formula Elementary analysis | ¹H NMR |
|---|---|---|---|---|
| 104 | −(CH₂)₂-[pyridine] | 133–134 | C₂₀H₂₅N₃O₃S<br>61.99  6.50  10.84<br>61.87  6.47  10.72 | (DMSO-d₆)1.0–2.4(4H, m)2.4–3.8<br>(9H, m)3.12(3H, s)7.22–7.42(3H, m)<br>7.48(1H, dt, J=8, 2)7.98(2H, d,<br>J=8)8.43(2H, m) |
| 105 | −(CH₂)₂-[pyridine with CH₃] | 189–191 | C₂₁H₂₇N₃O₃S·2HCl<br>53.16  6.16  8.86<br>52.88  6.10  8.77 | (DMSO-d₆)2.72(3H, s)3, 15(3H, s)<br>7.37(2H, d, J=8)7.71(1H, d, J=<br>8)7.75(1H, d, J=8)8.04(2H, d,<br>J=8)8.31(1H, t, J=8)10.55<br>(1H, s)11.40(1H, br)etc. |

TABLE 10

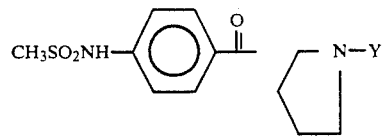

| Example | Y | Melting point | Structural formula Elementary analysis | ¹H NMR |
|---|---|---|---|---|
| 106 | —(CH₂)₂—(3-pyridyl) | 182–184 | C₁₉H₂₃N₃O₃S<br>61.11  6.21  11.25<br>61.13  6.25  11.08 | (CDCl₃—CD₃OD)2.0–2.32(2H, m)<br>2.4–3.2(8H, m)3.06(3H, s)<br>3.72–4.08(1H, m)7.16–7.38(3H, m)<br>7.60(1H, dt, J=8, 2)7.92(2H,<br>d, J=8)8.37(2H, m) |
| 107 | —(CH₂)₂—(6-methyl-2-pyridyl) | 151–153 | C₂₀H₂₅N₃O₃S·2(COOH)₂<br>50.79  5.15  7.40<br>50.76  5.09  7.19 | (DMSO-d₆)2.47(3H, s)3.14(3H, s)<br>7.13(2H, d, J=7)7.32(2H, d, J=<br>8)7.65(1H, t, J=7)8.00(2H, d,<br>J=8)etc. |
| 108 | —(CH₂)₂—(3,4-dimethoxyphenyl) | 142–143 | C₂₂H₂₈N₂O₅S<br>61.09  6.52  6.48<br>61.02  6.53  6.43 | (DMSO-d₆)1.8–2.2(2H, m)2.4–3.5<br>(8H, m)3.11(3H, S)3.70(3H, s)<br>3.72(3H, s)<br>3.80–4.08(1H, m)6.60–6.90(3H, m)<br>7.27(2H, d, J=8)7.94(2H, d,<br>J=8) |

TABLE 11

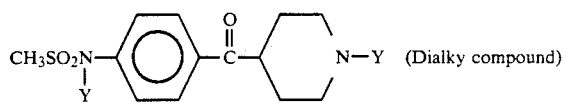 (Dialky compound)

| Example | Y | Melting point | Structural formula Elementary analysis | ¹H NMR |
|---|---|---|---|---|
| 109 | —(CH₂)₃CH₃ | 201–204 | C₂₁H₃₄N₂O₃S·HCl<br>58.50  8.20  6.50<br>58.65  8.07  6.43 | (DMSO-d₆)0.65–1.10(6H, m)1.05–2.30<br>(12H, m)2.60–3.95(9H, m)2.99(3H,<br>s)7.48(2H, d, J=8)7.96(2H, d,<br>J=8)10.45(1H, brs) |
| 110 | —CH₂—cyclohexyl | −257 (decomp.) | C₂₇H₄₂N₂O₃S<br>63.43<br>8.50  5.48<br>63.31<br>8.38  5.19 | (DMSO-d₆)0.63–2.40(26H, m)<br>2.60–4.00(9H, m)2.97(3H, s)<br>7.57(2H, d, J=8)8.05(2H, d,<br>J=8)9.95(1H, brs) |
| 111 | —CH₂—C(CH₃)=CH₂ | 138–141 | C₂₁H₃₀N₂O₃S·(COOH)₂<br>57.47  6.72  5.83<br>57.68  6.80  5.38 | (DMSO-d₆)1.63(3H, s)1.97(3H, s)<br>1.60–2.13(4H, m)2.50–3.78(5H, m)<br>3.04(3H, s)3.43(2H, s)4.28(2H,<br>s)4.67–4.90(2H, m)5.08(2H, s)<br>5.38(2H, brs)7.47(2H, d, J=8)<br>7.92(2H, d, J=8) |

TABLE 12

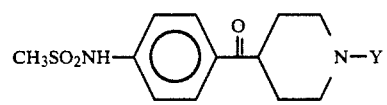

| Example | Y | melting point | structural formula | elementary analysis | ¹H NMR |
|---|---|---|---|---|---|
| 112 | —(CH₂)₂—(3-chlorophenyl)·HCl | ~193 (decomp) | C₂₁H₂₅ClN₂O₃S·HCl | 55.14  5.73  6.12<br>55.40  5.62  6.16 | (90 MHz, DMSO-d₆)δ1.73–2.23(4H, m)<br>2.67~3.91(9H, m)3.13(3H, s)7.17~7.49<br>(6H, m)8.00(2H, d, J=8.4) |

TABLE 12-continued

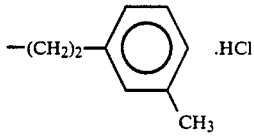

| Example | Y | melting point | structural formula | elementary analysis | | | ¹H NMR |
|---|---|---|---|---|---|---|---|
| 113 | —(CH₂)₂—⟨phenyl-CH₃⟩ .HCl | ~205 (decomp) | C₂₂H₂₈N₂O₃S. HCl | 60.47  60.33 | 6.69  6.63 | 6.41  6.52 | (90MHz, DMSO-d₆)δ1.63–2.20(4H, m) 2.30(3H, s)2.61–3.90(9H, m)3.12(3H, s) 6.96–7.25(4H, m)7.34(2H, d, J=8.8) 8.01(2H, d, J=8.8) |
| 114 | —CH₂—⟨tetrahydroquinolinyl⟩ | 178–180 | C₂₄H₃₁N₃O₃S | 65.28  64.95 | 7.08  6.87 | 9.52  9.62 | (90MHz, DMSO-d₆)δ1.35~2.03(8H, m) 2.03~3.40(10H, m)2.98(3H, s)6.97 (1H, dd, J=7.7, 4.6)7.12~7.38(3H, m) 7.81(2H, d, J=8.8)8.26(1H, dd, J=4.6, 1.6) |
| 115 | —(CH₂)₂—N⟨phthalimido-like⟩ | 257~259 | C₂₃H₂₆N₄O₅S. ½H₂O | 57.61  57.54 | 5.67  5.47 | 11.68  11.67 | (90MHz, DMSO-d₆)δ1.38~1.93(4H, m) 1.99~2.37(2H, m)2.43~3.51(5H, m) 3.11(3H, s)4.04(2H, brt, J=7)7.08~7.32 (4H, m)7.66(1H, t, J=7.5)7.94(3H, d, J=8.8) |

What is claimed is:

1. A compound having the formula

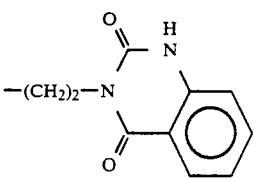

in which R¹ is a lower alkyl or a tolyl; R² is hydrogen, hydroxyl, a lower alkoxy or a lower alkyl; R³ is hydrogen, a lower alkyl, a lower alkenyl, a cycloalkyl or a cycloalkylalkyl; X is —CO—, —CH₂— or —CHOH—; g is an integer of 1, 2 or 3; h is an integer of 1, 2 or 3, with the proviso that the sum of g+h is the integer 3 or 4; A is (1) alkylene having 1 to 5 carbon atoms, (2) straight-chain alkylene having 1 to 5 carbon atoms in the chain and substituted with lower alkyl, phenyl or hydroxyl, (3) straight-chain alkenylene having 2 to 5 carbon atoms, (4) —(CH₂)$_k$—S—, wherein k is an integer of 2 to 5, or (5) —(CH₂)$_p$CO—, wherein p is an integer of 1 to 4 and B is 3-pyridazinyl, 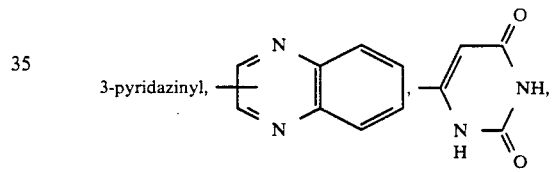

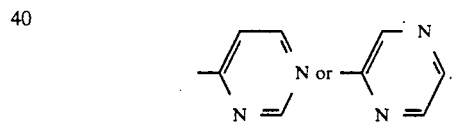

2. A compound according to claim 1, wherein X is a group of the formula —CO—.

3. A compound according to claim 1, wherein A is a group of the formula —(CH₂)$_n$—, in which n is an integer of 1 to 5.

4. A compound according to claim 1, wherein g and h are each 2.

5. A compound according to claim 1, wherein g is 3 and h is 1.

6. A compound according to claim 1, wherein g is 1 and h is 3.

7. A pharmaceutical composition which comprises a pharmacologically effective amount of the compound defined in claim 1 and a pharmacologically acceptable carrier.

8. A method for treating or preventing arrhythmia which comprises administering to a patient who requires such treatment a therapeutically acceptable amount of the compound defined in claim 1.

* * * * *